US006391452B1

(12) United States Patent
Antonsen et al.

(10) Patent No.: US 6,391,452 B1
(45) Date of Patent: *May 21, 2002

(54) COMPOSITIONS FOR NASAL DRUG DELIVERY, METHODS OF MAKING SAME, AND METHODS OF REMOVING RESIDUAL SOLVENT FROM PHARMACEUTICAL PREPARATIONS

(75) Inventors: Kris P. Antonsen, Berkeley; Rajiv Nayar, Richmond; Wei Wang; Margaret Caudle, both of Alameda; Michael A. Shearer, Fairfield; Neville M. Concessio, San Francisco, all of CA (US)

(73) Assignee: Bayer Corporation, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,463

(22) Filed: Jul. 17, 1998

Related U.S. Application Data

(60) Provisional application No. 60/052,964, filed on Jul. 18, 1997, and provisional application No. 60/056,625, filed on Aug. 20, 1997.

(51) Int. Cl.$^7$ .......................... B32B 15/02; B32B 17/02; B01J 13/02
(52) U.S. Cl. ................................ 428/402.2; 427/213.3; 427/213.31; 427/213.35; 264/4.1; 264/4.3; 264/4.6
(58) Field of Search .................. 264/4.1, 4.3, 4.6; 427/213.3, 213.31, 213.35; 428/402.2

(56) References Cited

U.S. PATENT DOCUMENTS

| | | | |
|---|---|---|---|
| 1,540,979 A | 6/1925 | Bloom | |
| 3,578,498 A | 5/1971 | Kite et al. | 127/71 |
| 4,847,091 A | 7/1989 | Illum | 424/455 |
| 5,204,108 A | 4/1993 | Illum | 424/434 |
| 5,240,694 A | 8/1993 | Gwaltney | 424/45 |
| 5,470,829 A | 11/1995 | Prisell et al. | 514/12 |
| 5,629,011 A | 5/1997 | Illum | 424/434 |
| 5,631,021 A * | 5/1997 | Okada et al. | 424/451 |
| 5,707,644 A | 1/1998 | Illum | 424/434 |
| 5,725,852 A | 3/1998 | Igari et al. | 424/85.7 |
| 5,879,712 A | 3/1999 | Bomberger et al. | 424/489 |
| 5,985,309 A * | 11/1999 | Edwards et al. | 424/426 |

FOREIGN PATENT DOCUMENTS

| | | |
|---|---|---|
| EP | 0314863 | 10/1989 |
| EP | 0391088 | 10/1990 |
| EP | 0362531 | 10/1999 |
| WO | 8703197 | 4/1987 |
| WO | 8809163 | 1/1988 |
| WO | 9010453 | 9/1990 |
| WO | 9306842 | 4/1993 |
| WO | 9400485 | 6/1994 |
| WO | 9427576 | 8/1994 |
| WO | 9527736 | 10/1995 |
| WO | 9603142 | 8/1996 |
| WO | 9627292 | 12/1996 |
| WO | 9640069 | 12/1996 |

OTHER PUBLICATIONS

Bodmeier, R. and J. W. McGinity, "Polylactic acid microspheres containing quinidine base and quinidine sulphate prepared by the solvent evaporation technique. I. Methods and morphology," J. Microencapsulation 4(4):279–288 (1987).

Franz, J., D. Pokorová, J. Hampl, and M. Dittrich, "Adjuvant efficacy of gelatin particles and microparticles," Intl. J. Pharmaceutics 168:153–161 (1998).

Greve, J. M., G. Davis, A. M. Meyer, C. P. Forte, S. C. Yost, C. W. Marlor, M. E. Kamarck, and A. McClelland, "The Major Human Rhinovirus Receptor is ICAM–1," Cell 56:839–847 (1989).

Hjertén, S., "The preparation of agarose spheres for chromatography of molecules and particles," Biochim. Biophys. Acta 79:393–398 (1964).

Jones, R. T., "Chapter 2. Gelatin: Structure and Manufacture," in *Hard Gelatin Development and Technology*, K. Ridgway, ed. (Pharmaceutical Press, London, 1987), pp. 13–30.

Marshall, A. S. and S. E. B. Petrie, "Thermal Transitions in Gelatin and Aqueous Gelatin Solutions," J. Photographic Science 28:128–134 (1980).

Raymond, G., M. Degennaro, and R. Mikeal, "Preparation of gelatin:phenytoin sodium microspheres: an *in vitro* and *in vivo* evaluation, " Drug. Development and Industrial Pharmacy 16(6):1025–1051 (1990).

Ugwoke, M. I., and R. Kinget, "Influence of processing variables on the properties of gelatin microspheres prepared by the emulsification solvent extraction technique," J. Microencapsulation 15(3):273–281 (1998).

Cortesi, R., E. Esposito, E. Menegatti, R. Gambari, and C. Nastruzzi, "Gelatin microspheres as a new approach for the controlled delivery of synthetic oligonucleotides and PCR–generated DNA fragments", Intl. J. Pharmaceutics 105:181–186 (1994).

Esposito, E., R. Cortesi and C. Nastruzzi, "Gelatin microspheres: influence of preparation parameters and thermal treatment on chemico–physical and biopharmaceutical properties", Biomaterials 17(20):2009–2020 (1996).

(List continued on next page.)

Primary Examiner—Nathan M. Nutter

(57) ABSTRACT

The present invention relates to pharmaceutical compositions for delivery of drugs intended to reside in the nose, compositions for nasal administration of drugs, e.g., antiviral agents, and particularly antiviral agents comprising the human major rhinovirus receptor, also known as intercellular adhesion molecule-1 (ICAM-1); to methods of making said nasal drug compositions, and to an improved process for the removal of residual solvent from pharmaceutical matrices.

25 Claims, 9 Drawing Sheets

OTHER PUBLICATIONS

Nastruzzi, C., C. Pastesini, R. Cortesi, E. Esposito, R. Gambari, and E. Menegatti, "Production and *in vitro* evaluation of gelatin microspheres containing an antitumour tetra–amidine", J. Microencapsulation 11(3):249–260 (1994).

Porter, H. F., P. Y. McCormick, R. L. Lucas, and D. F. Wells, "Section 20: Gas–Solid Systems", in *Chemical Engineers' Handbook, 5th ed.*, R. H. Perry and C. H. Chilton, eds. (McGraw–Hill, New York, 1973), pp. 20–1–20–121.

Rushton, J. H., E. W. Costich, and H. J. Everett, "Power Characteristics of Mixing Impellers: Part 1", in Chem. Eng. Progress 46(8):395–404 (1950).

Staunton, D. E., S. D. Marlin, C. Stratowa, M. L. Dustin, and T. A. Springer, "Primary Structure of ICAM–1 Demonstrates Interaction between Members of the Immunoglobulin and Integrin Supergene Families", Cell 52:925–933 (1988).

Welder, C. A., D. H. S. Lee, and F. Takei, "Inhibition of Cell Adhesion by Microspheres Coated with Recombinant Soluble Intercellular Adhesion Molecule–1", J. Immunol. 150(6):2203–2210 (1993).

Yoshioka, T., M. Hashida, S. Muranishi, and H. Sezaki, "Specific Delivery of Mitomycin C to the Liver, Spleen and Lung: Nano–and Microspherical Carriers of Gelatin", Intl. J. Pharmaceutics 81:131–141 (1981).

Al–Nakib, W., P. G. Higgins, G. I. Barrow, D. A. J. Tyrrell, K. Andries, G. Vanden Bussche, N. Taylor, and P. A. J. Janssen, "Suppression of Colds in Human Volunteers Challenged with Rhinovirus by a New Synthetic Drug (R61837)", Antimicrobial Agents and Chemotherapy 33(4):522–525 (1989).

Davis, S. S., L. Illum, J. G. McVie, and E. Tomlinson, eds., *Microspheres and Drug Therapy: Pharmaceutical, Immunological and Medical Aspects* (Elsevier, New York, 1984).

Florence, A. T., and Attwood (eds.), Polymers and Macromolecules, in *Physicochemical Principles of Pharmacy, 2nd ed.* (Chapman and Hall, New York, 1988), pp. 281–334.

Hardy, J. G., S. W. Lee and C. G. Wilson, "Intranasal drug delivery by spray and drops", J. Pharm. Pharmacol. 37:294–297 (1985).

Hayden, F. G. and J. M. Gwaltney, Jr., "Intranasal Interferon–$_2$ Treatment of Experimental Rhinoviral Colds", J. Inf. Dis. 150(2):174–180(1984).

Hayden, F. G., K. Andries, and P. A. J. Janssen, "Safety and Efficacy of Intranasal Pirodavir (R77975) in Experimental Rhinovirus Infection", Antimicrobial Agents and Chemotherapy 36(4):727–732 (1992).

Hayden, F. G., J. K. Albrecht, D. L. Kaiser, and J. M. Gwaltney, Jr., "Prevention of Natural Colds by Contact Prophylaxis with Intranasal $\alpha_2$–Interferon", New Eng. J. Med. 314(2):71–75 (1986).

Illum, L., "Chapter 5. Nasal Delivery of Peptides, factors affecting nasal absorption", in *Topics in Pharmaceutical Science* 1991, D. J. A. Crommellin and K. K. Midha, eds. (Medpharm, Stuttgart, 1992), Chapter 5, pp. 71–82.

Illum, L., "The nasal delivery of peptides and proteins", Trends in Biotechnology 9:284–289 (1991).

Kublik, H. and B–W. Mueller, "Rheological Properties of Polymer Solutions as Carriers for Nasal Drug Delivery Systems", Eur. J. Pharm. Biopharm. 39(5):192–196 (1993).

Shipper, N. G. M., J. C. Verhoef, and F. W. H. M. Merkus, "The Nasal Mucociliary Clearance: Relevance to Nasal Drug Delivery", Pharmaceutical Research 8(7):807–814 (1991).

von Itzstein, M., W–Y. Wu, G. B. Kok, M. S. Pegg, J. C. Dyason, B. Jin, T. V. Phan, M. L. Smythe, H. F. White, S. W. Oliver, P. M. Colman, J. N. Varghese, D. Michael Ryan, J. M. Woods, R. C. Bethell, V. J. Hotham, J. M. Cameron, and C. R. Penn, "Rational design of potent sialidase –based inhibitors of influenza virus replication," Nature 363:418–423 (1993).

Bachtsi, A. R. and C. Kiparissides, "An experimental investigation of enzyme release from poly(vinyl alcohol) crosslinked microspheres," J. Microencapsulation 12(1):23–35 (1995).

Illum, L., H. Jårgensen, H. Bisgaard, O. Krogsgaard, and N. Rossing, "Bioadhesive microspheres as a potential nasal drug delivery system," Intl. J. Pharmaceutics 39:189–199 (1987).

Leucuta, S. E., "The kinetics of in vitro release and the pharmacokinetics of miotic response in rabbits of gelatin and albumin microspheres with pilocarpine," Intl. J. Pharmaceutics 54:71–78 (1989).

Nakamura, M., S. Yamashita, Y. Tsume, T. Nadai, H. Sezaki, T. Kohno, Y. Tabata and Y. Ikada, "Potential efficacy of gelatin microspheres as a new adjuvant for oral vaccination," S. T. P. Pharma Sciences 8(1):67–73 (1998).

Nakaoka, R., Y. Tabata and Y. Ikada, "Potentiality of gelatin microsphere as immunological agent," Vaccine 13(7):653–661 (1995).

Narayani, R. and K. Panduranga Rao, "Biodegradable microspheres using two differrent gelatin drug conjugates for the controlled delivery of methotrexate," Intl. J. Pharmaceutics 128:261–268 (1996).

Öner, L. and M. J. Groves, "Optimizing of Conditions for Preparing 2–to 5–Micron–Range Gelatin Microparticles by Using Chilled Dehydration Agents," Pharm. Res. 10(4):621–626 (1993).

Shamblin, S. L., B. C. Hancock, and G. Zografi, "Water vapor sorption by peptides, proteins and their formulations," Eur. J. Pharmaceutics and Biopharmaceutics 45:239–247 (1998).

Tabata, Y. and Y. Ikada, "Synthesis of Gelatin Microspheres Containing Interferon," Pharm. Res. 6(5):422–427 (1989).

* cited by examiner

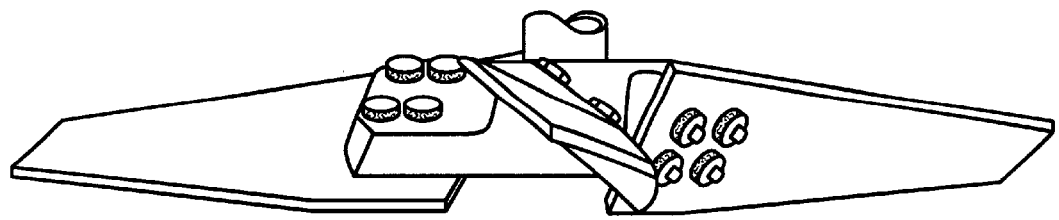
FIG._1A
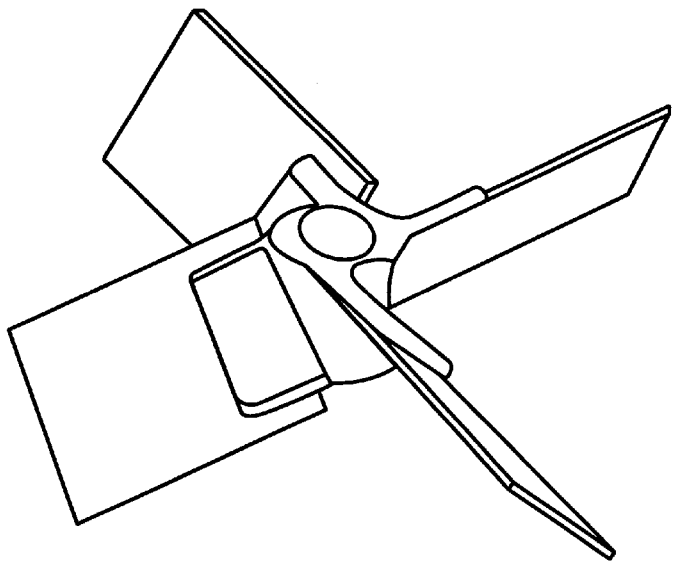
FIG._1B
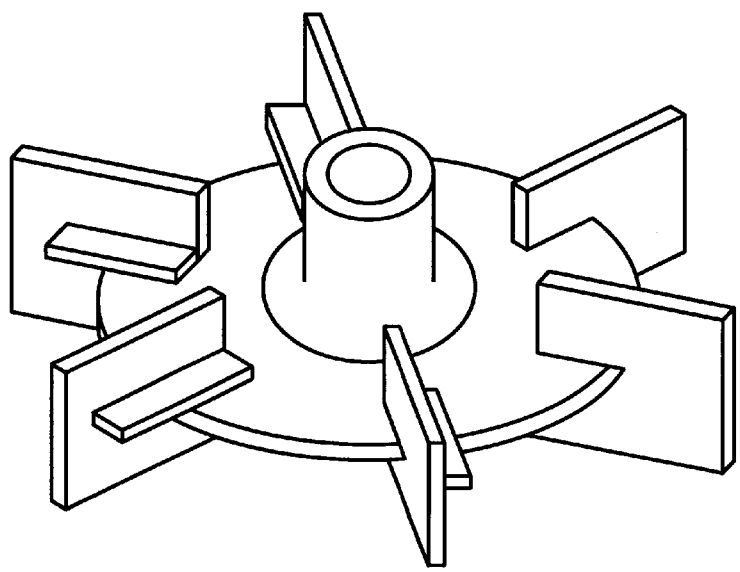
FIG._1C

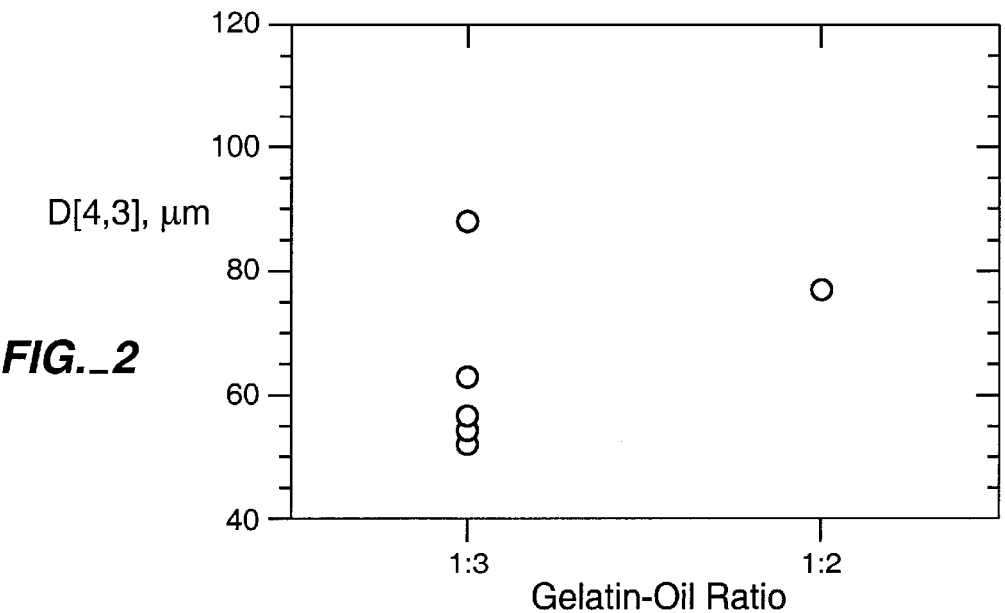
FIG._2
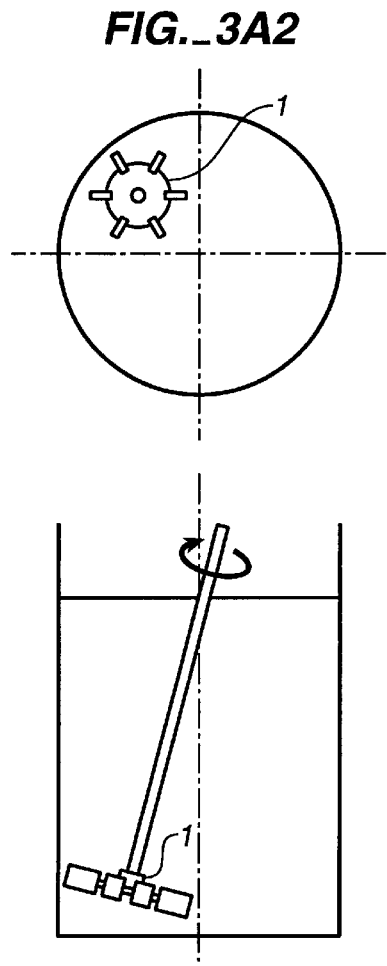
FIG._3A2
FIG._3A1
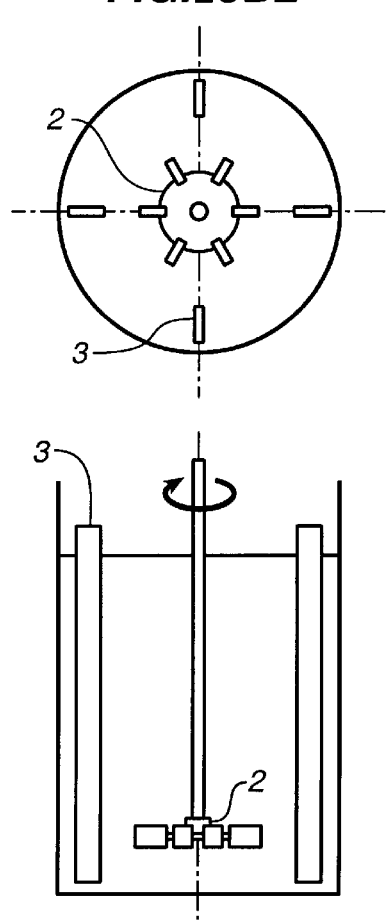
FIG._3B2
FIG._3B1

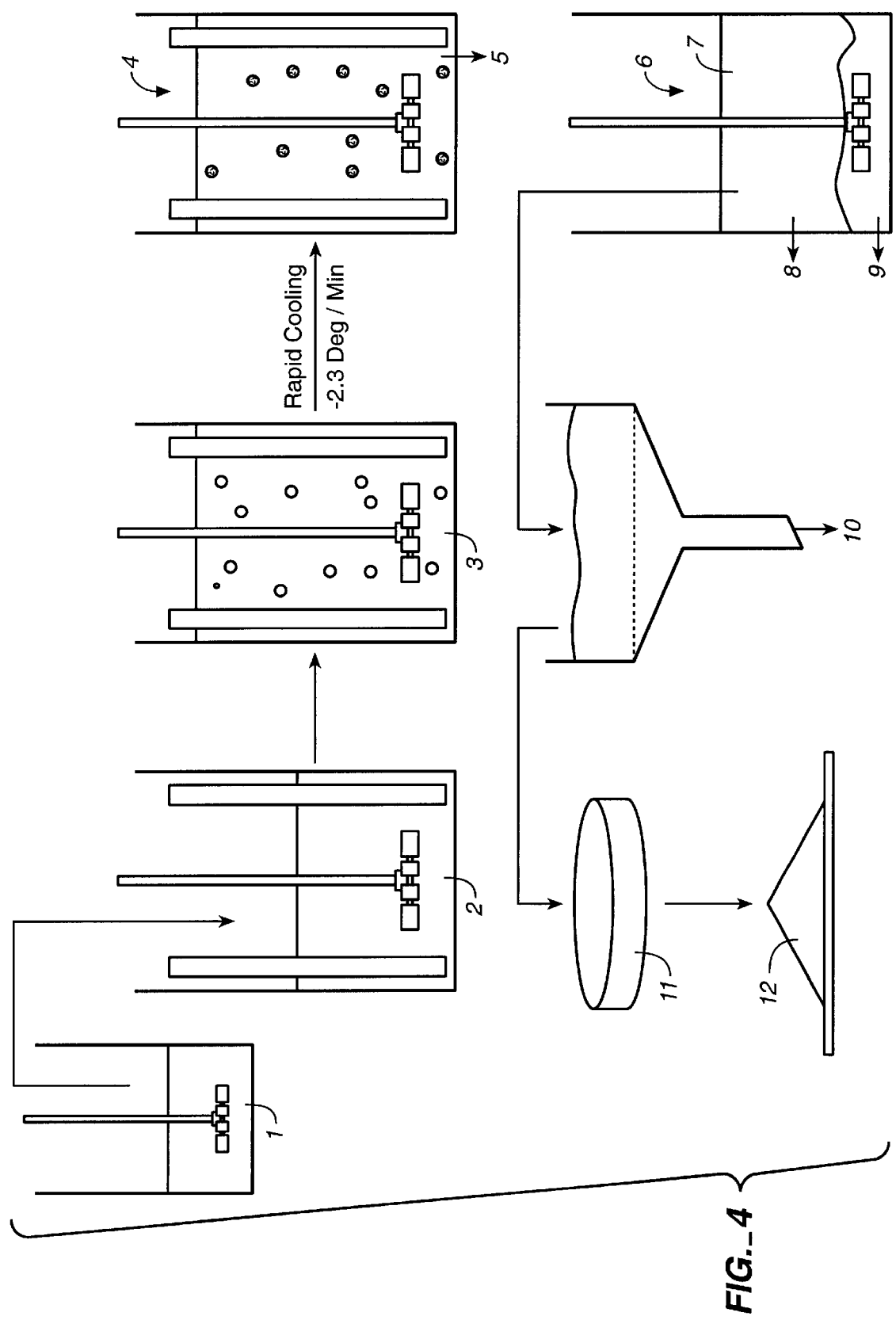
FIG._4

FIG._5A 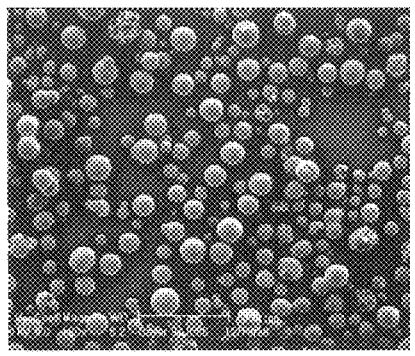
FIG._5B 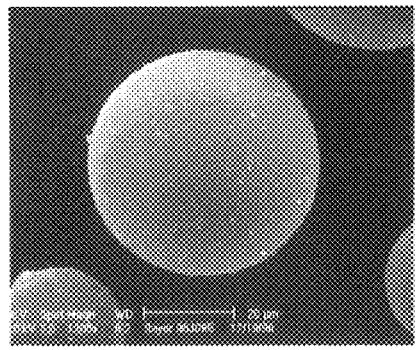
FIG._5C 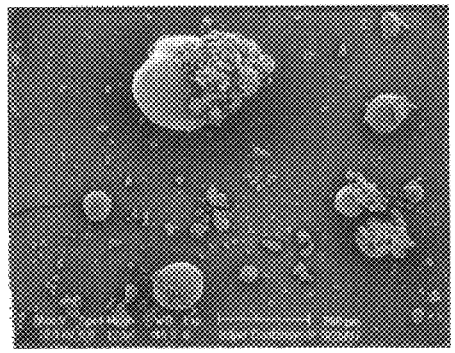
FIG._5D 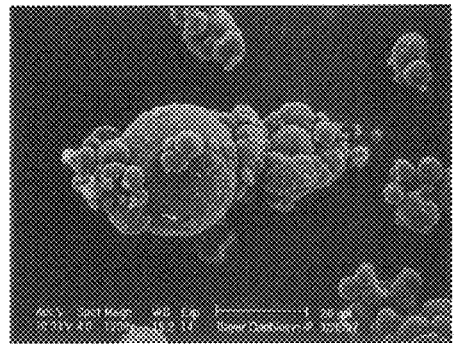

FIG._6A 50μm ⊢─┤
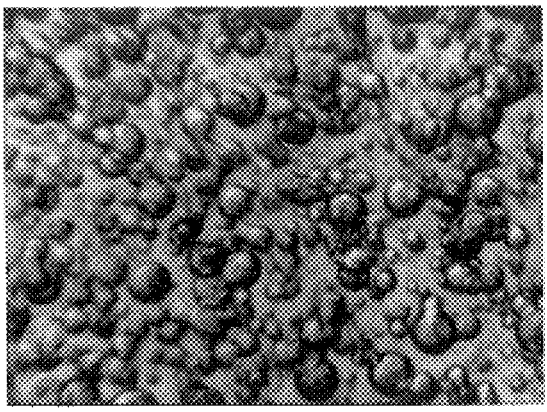
FIG._6B 50μm ⊢─┤
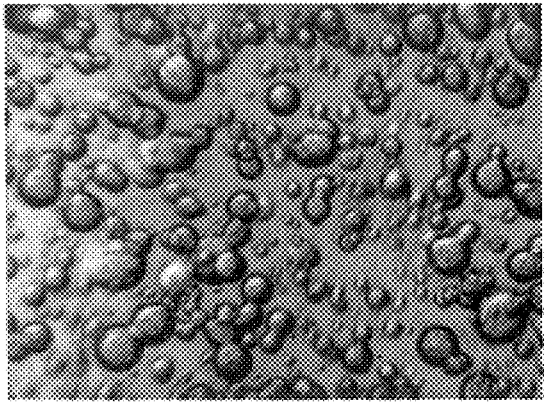
FIG._6C 50μm ⊢─┤
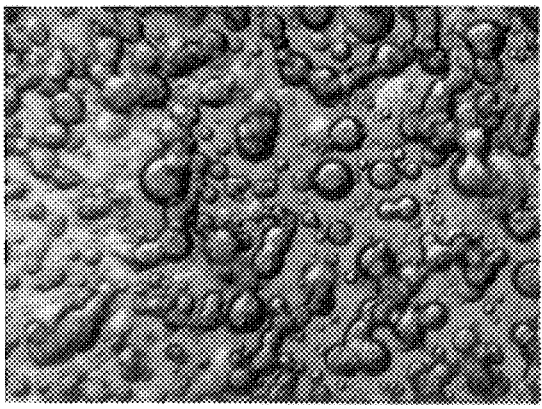
FIG._6D 50μm ⊢─┤
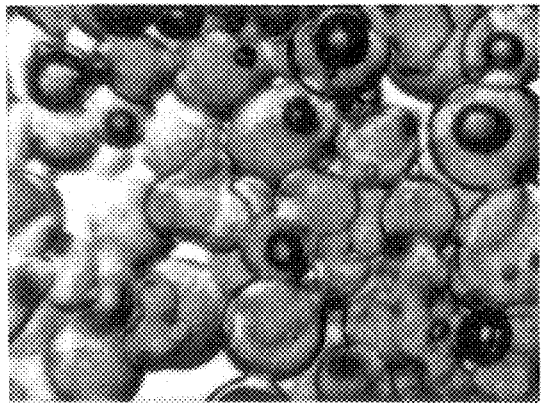

FIG._7A 50μm ⊢⊣  FIG._7B 50μm ⊢⊣
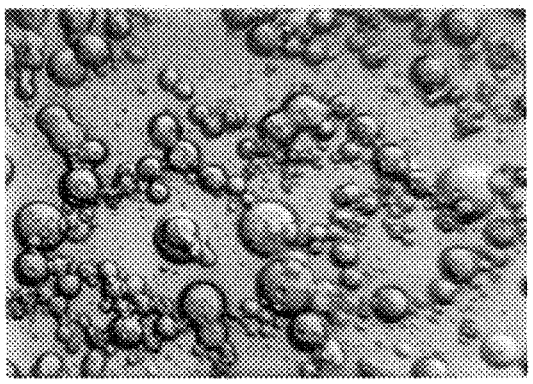 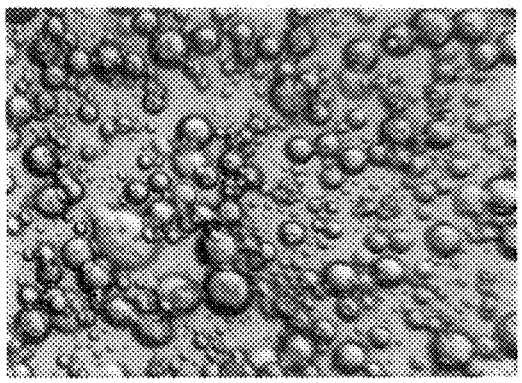
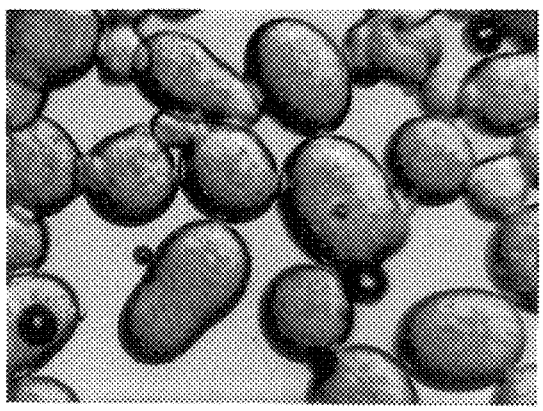 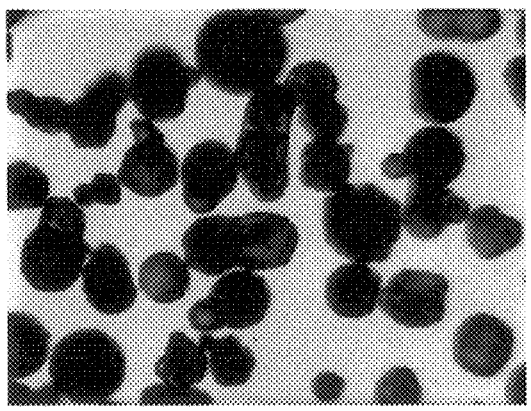
FIG._7C 50μm ⊢⊣  FIG._7D 50μm ⊢⊣

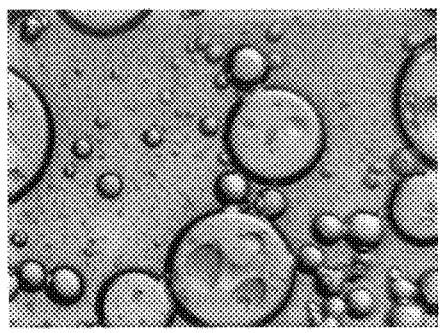
FIG._8A
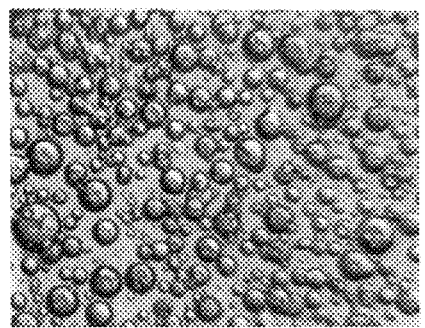
FIG._8B
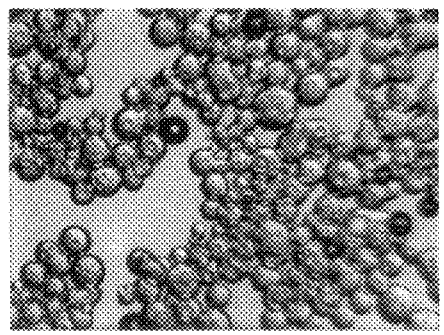
FIG._8C
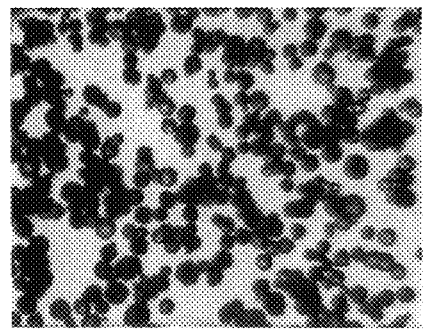
FIG._8D

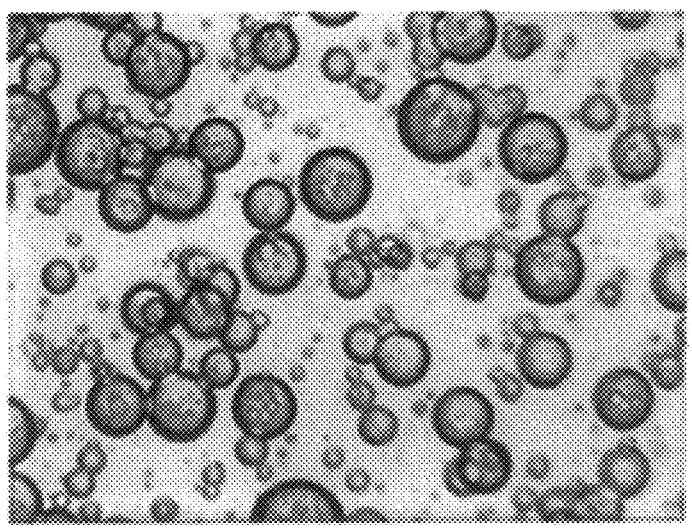
FIG._9A
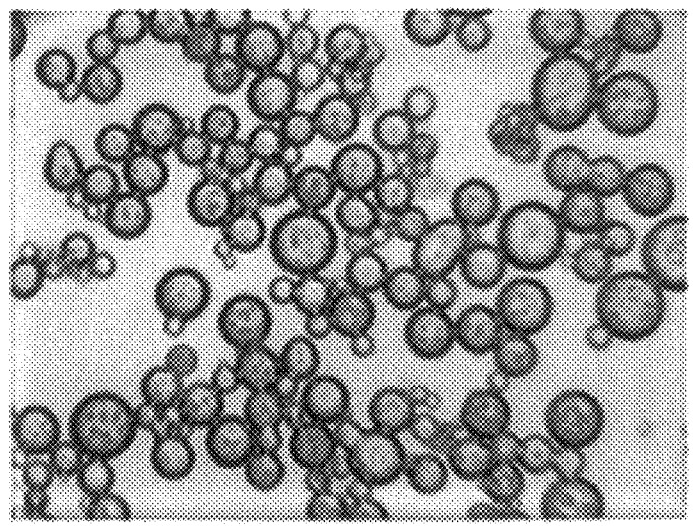
FIG._9B
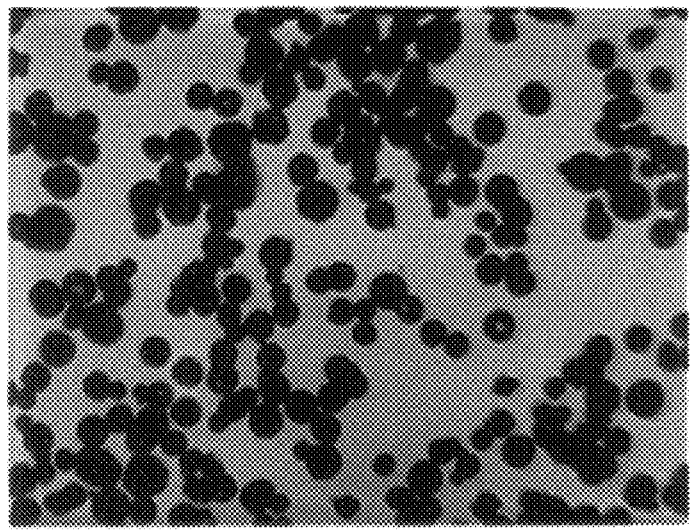
FIG._9C

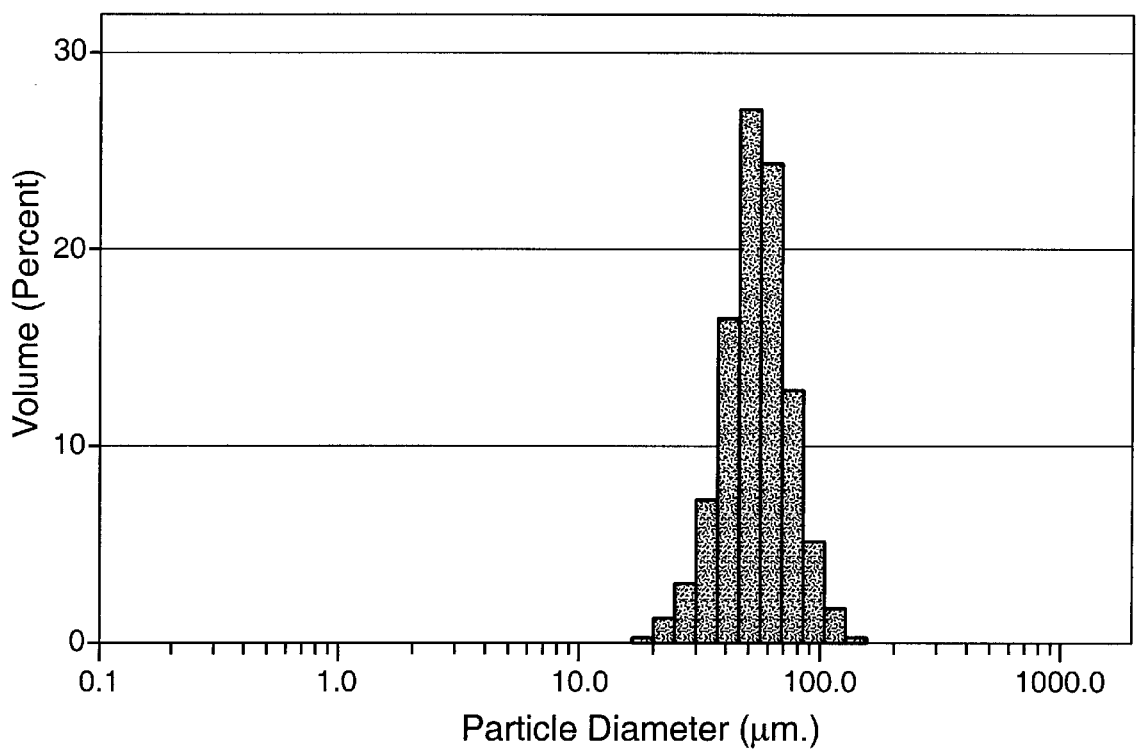
FIG._10

COMPOSITIONS FOR NASAL DRUG DELIVERY, METHODS OF MAKING SAME, AND METHODS OF REMOVING RESIDUAL SOLVENT FROM PHARMACEUTICAL PREPARATIONS

This application claims the benefit of U.S. Provisional No. 60/052,964 filed Jul. 18, 1997 and 60/056,625 filed Aug. 20, 1997.

BACKGROUND

1. Field of Invention

The present invention relates to compositions for delivery of drugs intended to reside in the nose. The invention also pertains to methods of making such nasal drug delivery compositions and to improved methods of removing solvents from pharmaceutical preparations.

2. Background

A number of intranasal preparations are known which are specifically designed to deliver drugs across the nasal mucosal membranes to effect systemic drug administration. However, there remains a need for intranasal preparations specifically designed to retain the drugs for extended periods of time in the nose without crossing the mucosal membranes.

Cortesi, R., Esposito, E., Menegatti, E., Gambri, R., and Nastruzzi, C., "Gelatin Microspheres as a New Approach for the Controlled Delivery of Synthetic Nucleotides and PCR-Generated DNA Fragments", Int. J. Pharm. 105:181–6 (1994), disclose a gelatin solution emulsified in isopropyl palmitate as the oil phase (without surfactant). Gel beads are formed by cooling the emulsion, and these are then washed with acetone and collected on a sintered glass disk. The mean volume particle diameter is 22 $\mu$m, with a range of 5–42 $\mu$m. As particles below 10 $\mu$m tend to deposit in the lungs, this range of particle size is not suitable for administration of pharmaceuticals intended for retention in the nose.

Illum et al., PCT/GB95/01735 describe a drug delivery composition for nasal administration comprising ICAM-1 and bioadhesive compositions comprising chitosan, a liquid polymeric material, or a variety of water-swellable microspheres, including gelatin. Ilium discloses the concept of emulsifying a warm aqueous solution of gelatin and ICAM-1 in a vegetable oil containing a surfactant, followed by thermal gelation, hardening with acetone, harvesting the ICAM/gelatin microspheres, and drying.

However, the processes taught by Ilium for the production of gelatin microspheres and the resulting product are not desirable for commercial scale pharmaceutical use. The process requires large amounts of oil and acetone. The resulting product has been found to contain mainly aggregates of small primary particles. These aggregates tend to deaggregate during handling, resulting in mixtures of fragments and non-aggregated particles with about 3.5% by volume of particles with volume diameters below 10 $\mu$m. Particles below 10 $\mu$m volume diameter are not suitable for administration of drugs intended for nasal retention, as they tend to enter the lower airway and lungs, which is not desirable from either a safety or commercial standpoint.

Accordingly, it is desirable to provide a pharmaceutical preparation for delivery of drugs to the nose that maintains biological activity and physical integrity, exhibits extended intranasal residence time, and allows sustained release of active ingredient in the nasal cavity. The desired characteristics for an intranasal formulation include:

(1) a pharmaceutically acceptable formulation with respect to process consistency, scalability, and GRAS (generally regarded as safe) components;

(2) sustained release of active drug over time;

(3) high quality and activity of released drug;

(4) restricted particle size range of volume diameter 10–100 $\mu$m, preferably 20–80 $\mu$m, to minimize concerns about lung delivery;

(5) lack of irritation to the mucociliary apparatus;

(6) convenient and reproducible administration into the nasal cavity;

(7) dry powder based;

(8) stability over time without refrigeration; and (9) residual solvent levels at or below pharmaceutically acceptable levels.

Criteria for a commercially suitable process for producing such a product include minimal solvent consumption and demonstrated scalability to at least 300 g.

One problem commonly found in pharmaceutical compositions in which the production process involves solvents is unacceptably high levels of residual solvent in the final product, so that the product does not meet safety and regulatory requirements. Traditional methods of removing solvents are frequently unsatisfactory. For example, evaporation under vacuum at room temperature may be inadequate and at elevated temperatures may cause degradation of the active ingredient. The alternative technique, extraction by supercritical fluid, is not always effective when applied to dry powders. Thus, there is a need for an improved method of removing residual solvents from pharmaceutical formulations.

The present invention provides these and other advantages.

SUMMARY OF INVENTION

The present invention provides an improved process for production of pharmaceutical gelatin-based microsphere compositions comprising one or more drugs to be delivered to and retained in the nose, and the drug-containing microspheres produced by this process. The invention also concerns improved methods of removing solvents from dry powder pharmaceutical compositions.

In general, the process for making the microsphere/drug composition comprises the following steps:

a) preparing a low-salt or salt-free aqueous solution of gelatin and the drug to be delivered at a temperature above the gelation temperature of the gelatin;

b) preparing a solution of a suitable oil and a suitable surfactant;

c) emulsifying a mixture of the solution of step (a) and the solution of step (b) to generate a water-in-oil emulsion wherein the volume ratio of (a):(b) is between 1:2 and 1:10;

d) continuing emulsification until the target droplet size is achieved;

e) thereafter reducing the temperature of said emulsion to below the gelation temperature of the gelatin at a controlled rapid rate to achieve gelation before droplet coalescence, thus allowing the formation of gelatin microspheres associated with drug at the desired particle size;

the emulsion in steps (c, d) and (e) above being mixed at the maximum rate consistent with a low-vortex or vortex-free circulation pattern;

f) separating the drug-containing microspheres from the oil/surfactant phase; and g) dehydrating the drug-containing microspheres to produce a dry powder.

The invention also comprises an improved method for removing residual solvent from pharmaceutical matrices such as dry powders by contacting said matrices with a humidified stream of a suitable gas under conditions which permit residual solvent to be entrained in the gas, and then drawing off the gas. This can be done in discreet batches or as part of a continuous flow process.

The resulting product is a free-flowing powder comprising gelatin microspheres associated with drug, with a volume particle diameter of between 40–60 µm and wherein a preponderance of the microspheres exist as unaggregated individual particles, rather than as aggregates of smaller particles.

The invention further comprises an intranasal drug delivery system comprising the above gelatin microspheres in association with a drug to be delivered to and retained in the nose.

DRAWINGS

FIG. 1 shows impellers suitable for use in the present invention: (A) the A310 is a high-efficiency axial flow impeller; (B) the A200 is a four-blade axial flow impeller; and (C) the R100 is a radial-flow impeller. All are manufactured by Lightnin Equipment.

FIG. 2 shows results of the gelatin:oil ratio studies of Example 2.

FIG. 3 shows the preferred position of the impellers in the emulsification step for volumes below 3 L (FIGS. 3A1 and 3A2) and for volumes of 3 L and above (FIGS. 3B1 and 3B2). FIG. 3A1, side view; FIG. 3A2, top view; FIG. 3B1, side view; FIG. 3B2, top view. (1), 3" radial impeller (top left quadrant, 12 deg. to vertical); (2), 4" radial impeller; (3), baffles.

FIG. 4 shows a schematic representation of a batch emulsification process suitable for preparation of microspheres. (1) gelatin solution (50° C.); (2) oil/Span mixture (50° C.); (3) water in oil emulsion; (4) acetone; (5) solid microspheres suspended in oil; (6) acetone washings; (7) oil/acetone; (8) acetone; (9) microspheres; (10) vacuum; (11) 75 µm mesh sieve; (12) dried microspheres.

FIG. 5 shows scanning electron micrographs showing structure of tICAM(453)/gelatin microspheres made by the process of Example 8 (panels A and B) and by the method of Illum et al., supra (panels C and D). The mean volume particle diameter of the preparation in panels A and B is 46.4 µm, with 0.5% of particles having a volume particle diameter >100 µm and undetectable levels of particles having a volume particle diameter <10 µm. In contrast, the mean volume particle diameter for panels C and D is 123 µm, with 39% >100 µm and 33% <10 µm.

FIG. 6 shows appearance of the emulsion droplets and microspheres at various stages during the batch emulsification process of Example 15 using baffles, gradual cooling, and high mixing speed: (A) emulsion droplets at 50° C.; (B) emulsion droplets at 40° C.; (C) emulsion droplets at 35° C.; and (D) emulsion droplets at 30° C.

FIG. 7 shows appearance of the emulsion droplets and microspheres at various stages during the batch emulsification process of Example 15 using baffles, moderate cooling, and high mixing speed: (A) emulsion droplets at 625 rpm (1 min); (B) emulsion droplets at 625 rpm (20 min); (C) cooled emulsion (<15° C.); and (D) microspheres (washed and dried).

FIG. 8 shows appearance of the emulsion droplets and microspheres at various stages during the batch emulsification process of Example 15 using baffles, rapid cooling, and a high mixing speed: (A) emulsion droplets immediately following gelatin addition at 375 rpm; (B) emulsion droplets following mixing at 625 rpm for 20 min; (C) gelatin microspheres suspended in oil following mixing for one hour below 15° C. at 625 rpm; and (D) gelatin microspheres following washing, filtration and vacuum drying.

FIG. 9 shows appearance of the emulsion droplets and microspheres at various stages during the low mixing speed process of Example 15 using baffles and rapid cooling: (A) emulsion at 425 rpm (30 min); (B) cooled emulsion at 15° C.; and (C) microspheres (washed and dried).

FIG. 10 shows typical particle size distribution obtained by laser particle sizing of microspheres generated by the rapid cooling method of Example 15, using baffles, higher impeller height, and lower mixing speed.

DETAILED DESCRIPTION OF INVENTION

1. Method of making gelatin microspheres (see FIG. 4):

Preparation of aqueous solution of gelatin and drug:

An aqueous solution of gelatin and drug is prepared. Neither gelatin grade nor gelatin concentration are critical to the size of the final microspheres. Gelatin should be food-grade, preferably at least NF grade. The gelatin should have a bloom strength of at least 80, and preferably of ≧150. A bloom strength of 250 is most preferred because its properties are fairly consistent from batch to batch and it is available year round. Its color is lighter and has a fainter odor than lower-quality gelatin grades. Higher bloom strengths provide superior color, odor, and nasal residence time in the final product. Suitable gelatin is, e.g. P-8 grade, 250 bloom, obtained from Hormel Foods (Austin, Minn.). The concentration of gelatin may conveniently be in a range of from about 1% to about 30% (w/w). Within this range, higher gelatin concentrations lead to reduced solvent and oil consumption, but the total solids content in the aqueous solution (including gelatin and drug to be delivered) should not exceed 30% (w/w). Because gelatin concentration did not appear to affect the ultimate volume particle diameter, 20%, which is the highest easily-handled concentration based on viscosity, is preferred.

The drug to be delivered may be any suitable chemical or biological pharmaceutical agent that is capable of being dissolved or suspended in a gelatin solution and that is insoluble in the oil and insoluble in the dehydrating solvent used in the process. Examples of suitable drugs include but are not limited to, e.g., small chemical entities; proteins, peptides, and polypeptides (e.g. ICAM-1 and other antiviral agents; vaccines, antigens, antibodies; lymphokines, and fragments of any of the foregoing; nucleotides (e.g. genes, DNA, RNA, and fragments of any of the foregoing) carbohydrates, etc. The concentration of the drug to be delivered is similarly determined by the total allowable concentration of the loaded solids.

The aqueous solution of gelatin and drug may be prepared by any convenient means. Solutions of gelatin and drug may be prepared individually and then mixed, or either the gelatin or the drug may be added to a solution of the other. Persons skilled in the art will understand that buffering or adjustment of the pH may be needed to protect the drug during processing. Also, for protein drugs it is preferable that the aqueous solution be low-salt or salt-free to avoid precipitating the protein. By "low salt" is meant <200 mOs/kg.

When the drug is ICAM-1, a solution of ICAM-1 in histidine buffer, pH 7, is conveniently prepared and added to an aqueous solution of gelatin. L-histidine is obtained from, e.g., Calbiochem Corp. The term "ICAM" as used herein is intended to refer to ICAM-1 and any fragments, analog or derivative of ICAM-1 which retains the ability to bind to human rhinovirus of the major receptor group and inhibit infectivity. The ICAM may be prepared as set forth in Example 1 below.

Gelatin-containing solutions should be held at a temperature above the gelation temperature of the gelatin. For a gelatin with a bloom strength of 250, this means at 40° C. or higher.

Preparation of solution of oil and surfactant:

The oil is preferably a refined oil, e.g. mineral or vegetable oil, preferably food-grade or NF grade vegetable oil. Examples of suitable vegetable oils are corn, soybean, and safflower. Hyperrefined vegetable oils from which color bodies, hydrophilic substances, and natural surfactants have been removed do not work as well as less refined oils in this procedure. Corn oil and soybean oil are preferred; corn oil is particularly preferred because it is more economical. Suitable corn oil is e.g. NF grade as obtained from, e.g., Ruger Chemical Co. (Welch, Holme and Clark).

Examples of suitable surfactants are Span 80 (sorbitan monooleate, obtained from Ruger Chemical Co., ICI Americas Inc.), lecithin, and pluronic L 1011 (BASF). Span 80 is preferred. In general, a hydrophilic-lipophilic balance (HLB) of 4–6 is desired. Surfactants with HLB values of 3 or below (e.g. glyceryl monooleate, sorbitan trioleate) are less effective. A surfactant concentration of 0.1% is too low, 1% is functional, and higher concentrations provide no further improvement in the result.

4) Emulsification:

The aqueous solution of gelatin and drug is emulsified with the solution of oil and surfactant is emulsified to generate a water-in-oil emulsion.

Methods of emulsification are well-known in the art. Generally, the aqueous gelatin/drug solution is gradually added to the oil/surfactant solution with stirring or mixing. Proper agitation during emulsification is required to achieve the desired mean volume particle diameter (40–60 $\mu$m). It is possible to use a variety of stirrers or impellers, but it is preferred to minimize the formation of a vortex to avoid air entrainment. This can be achieved through the use of baffles or correct positioning of the impeller. Initial specific power consumption is preferably at least 1.4 watts/L. High-shear mixing should be avoided. Mixing conditions affect the final product and so care must be taken to reproduce mixing conditions to insure reproducibility of the final product.

The volume ratio of gelatin/drug solution to oil/surfactant solution affects the quality of the resulting product. Preferably the volume ratio of gelatin/drug solution to oil/surfactant solution is between 1:2 and 1:10. Larger ratios are desirable because the emulsion volume, and the oil and solvent requirements, are reduced. However, the mean volume particle diameter rises gradually with volume ratios up to 1:2. At higher ratios, the mean volume particle diameter rises dramatically, and at even higher ratios, emulsion inversion takes place, making particle formation impossible. Volume ratios of 1:2 to 1:5 are preferred; 1:3 to 1:4 are particularly preferred.

Emulsification is continued until the target droplet size is obtained. Droplet size is monitored by methods known to those in the art, e.g. by optical microscopy. Droplets of 20–80 $\mu$m are preferred; 40–60 $\mu$m are particularly preferred. For a volume of 8 L, a mean volume particle size of approximately 50 $\mu$m can be achieved in approximately 30 min (±10 min).

5) Cooling:

The temperature of the emulsion is reduced to below the gelation temperature of the gelatin at a controlled rapid rate to achieve gelation before droplet coalescence, thus allowing the formation of gelatin microspheres with associated drug at the desired particle size. For example, for gelatin of bloom strength of 250, the emulsion is cooled to a temperature of 23° C. or lower.

Preferably the cooling rate is between 1–4° C./min. A cooling rate of between 2.0–2.5° C./min is particularly preferred.

Separating the drug/microspheres from the oil/surfactant phase:

In general, separation is most efficient if the microspheres are separated from as much of the oil as possible at the outset. This can be done by physical means, such as allowing the microspheres to settle under gravity or by centrifugation followed by decantation. Separation can also be accomplished by washing with suitable solvents. It is important that the emulsification be agitated gently during the washing process. If washing is used, there are several possible alternatives to remove the oil:

a) In the first method, the oil is removed by washing first with ½ volume hydrocarbon solvent such as heptane, then by washing with a water-miscible solvent such as acetone.

The hydrocarbon solvent is chosen as follows:

i) it should be miscible with both the oil and the water-miscible wash chosen below;

ii) it should not dissolve appreciable water; and iii) its density should be less than mixtures of water and the water-miscible solvent containing up to 20% water.

The hydrocarbon wash reduces the oil phase viscosity and density, allowing the microspheres to settle easily with gravity. This permits a large portion of the hydrocarbon phase to be decanted immediately. A single wash with 0.5 emulsion volumes is sufficient. The wash is carried out by brief stirring (5 min) at room temperature. Two such washes are sufficient to remove a majority of the oil.

The remaining washes are with a water-miscible solvent such as acetone (HPLC grade, J. T. Baker) or low molecular weight alcohols. If the hydrocarbon is chosen according to the criteria set forth above, the initial water-miscible wash will lead to three phases (1) the gelatin microspheres, (2) a liquid phase (mostly water-miscible wash), and (3) another liquid phase floating on the water-miscible wash and containing mostly the hydrocarbon and the remaining oil. This splitting of the two liquid phases is a consequence of extracting the water from the gelatin microspheres. The two organic phases separate easily from each other and from the solids. An advantage of this approach is that the microspheres are transferred into the water-miscible solvent-rich phase, where they will remain throughout the rest of the washes. Typically the hydrocarbon-rich phase is eliminated after the initial water-miscible solvent wash.

(b) The second method is to wash only with water-miscible solvent. This process is carried out using sequential stirring, settling, and decantation steps as above. This has the virtue of requiring only one solvent, but is somewhat more complex because the initial water-miscible wash again results in a splitting of the liquid into two phases. In this case, however, the oil-rich phase is the lower one, and the beads are not separated immediately from the oil and surfactant. The acetone, because it also acts as a solvent, for water, does not appreciably reduce the oil-phase viscosity, and ordinarily at least two water-miscible washes of 1 emulsion volume each are necessary to remove the oil phase. Phase separation is slower than when hydrocarbon is used as in (a) above.

Dehydrating the drug/microspheres to produce a dry powder:

The now-dehydrated gelatin/drug microspheres, suspended in water-miscible solvent, are collected. Methods of separating the microspheres from the water-miscible solvent are well-known to those in the art. Examples of suitable means are filtration using e.g. a Buechner funnel or centrifugation using ordinary or basket centrifuges.

Key factors in the above process are choice of oil, surfactant type, surfactant concentration, gelatin/oil ratio, the choice of mixing conditions, the thermal history of the emulsion and the cooling rate (temperature profile), and the washing method (including solvent choices).

The process of the present invention is suitable for scale-up more than 100× over that described by Illum et al.

An advantage of the present process is that the microsphere product has no particles having volume particle diameters less than 10 $\mu$m as measured by laser light scattering analysis. In the laser light scattering technique, the angular variation in intensity of light scattered from a plume of the particles in air is measured, using as a light source a laser of defined wavelength. The scattering data are deconvoluted to provide a volumetric particle size distribution. Instruments suitable for making these measurements are known to those skilled in the art and are available from e.g. Malvern Instruments, Southboro, Mass. The desired particle size range is achieved by use of high-bloom strength gelatin (preferably at least 150, most preferably 250 or greater), use of a low-salt or salt-free buffer for the aqueous gelatin/drug solution, consistent low-vortex or vortex-free stirring during emulsification to achieve consistent droplets of the target size, and rapid cooling upon attainment of desired droplet size to prevent aggregation. The improved process eliminates the need for a centrifuge and facilitates large batch processing. It also uses less solvent, is more efficient, costs less, and results in better product than the prior art processes.

The foregoing processes can be conducted either as batch processes or as continuous or in-line processes according to techniques and using equipment known to those skilled in the art, and person skilled in the art will be able to make appropriate adjustments and modifications to implement each of these techniques.

II. Reducing the residual solvent to pharmaceutically acceptable level

The invention further comprises a novel method of removing volatile solvent from a pharmaceutical matrix. The process involves contacting said pharmaceutical matrix with a suitable humidified gas under conditions which permit residual solvent to be entrained in the gas, and removing the solvent/gas mixture. Preferably, the humidified gas is passed through a fluidized bed of the pharmaceutical matrix.

The pharmaceutical matrix may be any pharmaceutical formulation, including but not limited to, e.g., beads, polymer or nonpolymer processed materials, drug-related raw materials, excipients and final products including biopharmaceuticals, including dry powder microspheres such as gelatin microspheres prepared according to the above process, and oil-based microspheres such as liposomes known in the art. The invention is particularly suitable for use with matrices which tend to physically trap entrained solvent within the matrix, so that procedures such as heat or vacuum drying do not effectively remove the solvent.

The solvent may be any residual volatile solvent remaining after the basic preparation process. Examples of solvents commonly used in the preparation of pharmaceutical formulations include water, acetone, and aliphatic alcohols (e.g. methanol, ethanol, isopropyl alcohol), DMSO, chloroform, methylene chloride etc.

The gas may be any suitable gas which is nonreactive with the pharmaceutical formulation and which is capable of removing and carrying the solvent. Examples of suitable gases are air, nitrogen, argon, and carbon dioxide.

The relative humidity in the gas should be from about 85 to about 96%. The purpose of the humidity is to retain sufficient moisture within the pharmaceutical matrix. For matrices which tend to trap solvent, low moisture content inhibits escape of the solvent. When the solvent is water, lower relative humidities should be used. Humidities of 0–50% are preferred, depending on the water sorption and desorption properties of the matrix.

To increase the moisture content of the pharmaceutical matrix, the matrix could simply be placed in a gas-tight chamber with an appropriate salt solution to obtain a specific high humidity. However, the evaporated solvent would not be able to leave the closed chamber and therefore, would equilibrate with the solvent adsorbed in the matrix. In addition, stagnant dry matrix easily aggregates under high relative humidities. To continuously remove the evaporated solvent, humidified gas could be passed over the matrix but three problems would still exist: (1) a matrix such as a powder would be difficult to contain; (2) dry matrix could be stagnant and could form aggregates; and (3) the evaporated solvent could be hazardous and difficult to control.

To overcome these problems, a fluidized bed is prepared according to methods known to those skilled in the art, see, e.g., Porter, H. F., McCormick, P. Y., Lucas, R. L., and Wells, D. F., "Gas-Solid Systems," in *Chemical Engineers' Handbook,* 5th ed., R. H. Perry and C. H. Chilton, eds. (McGraw-Hill, New York, 1973). Conveniently, a column such as a chromatography column may be used. The matrix containing the residual solvent is loaded into the column and humidified gas is passed into the bottom of the column and through the pharmaceutical matrix in order to fluidize the matrix bed. Advantages to using such a column include: (1) the humidified gas can be evenly distributed through the whole area of the bottom filter support, exposing the pharmaceutical matrix homogeneously to the gas stream, and (2) the column can be easily dismantled for sample loading, unloading, and cleaning. Because of the gas flow, the pharmaceutical matrix is completely fluidized inside the column. The continuous fluidization reduces aggregation of dry matrix.

Residual water is then removed by passing dry gas through the matrix and removing the humidified gas. For this purpose "dry" means having less than 50% relative humidity.

Apparatuses suitable for use in the present invention are available commercially from, e.g., Fluid Air Inc., Aurora, Ill.; Niro Inc., Columbia, Md. Other variations will be apparent to those skilled in the art, for example methods of modifying the apparatus and procedure as necessary for various matrices and batch sizes.

When used in combination with the above method for making drug/gelatin microspheres using acetone as a solvent, a humidity of 92% at room temperature is capable of reducing residual acetone level to 200 ppm or below within 8 hours. It is believed that acetone is adsorbed and bound strongly in the gelatin matrix by hydrogen bonding, which prevents its removal from the polymer under relatively high vacuum and/or even at temperatures higher than its boiling point. By increasing the moisture content of the gelatin, the hydrogen-bound acetone molecules are replaced quickly by water molecules. The decreased glass transition temperature of gelatin at higher moisture contents also increases the rate of acetone diffusion out of the gelatin matrix.

The result is a dry powder having a pharmaceutically acceptable level of residual solvent.

III. Product

The resulting product is a free-flowing dry powder comprising gelatin microspheres containg the desired drug. Specifically, the following parameters are preferred:

| | |
|---|---|
| Mean volume particle diameter | 20–80 μm |
| Span* | <1.0 |
| % of particles with >100 μm volume particle diameter | <10% |
| % of particles with <10 μm volume particle diameter | <1% (by laser light scattering) |
| Potency of released drug | active |
| Process scale (dry-weight basis) | >100 g |
| When the solvent is acetone, preferred residual level | <250 ppm |

[*Span is a measure of the particle size distribution calculated from percentiles.

$$\text{Span} = \frac{D(v, 0.9) - D(v, 0.1)}{D(v, 0.5)} \quad (1)$$

where, D(v, 0.9), D(v, 0.1) and D(v, 0.5) are the 90th, l0th and 50th percentile volume particle diameter of the microspheres, respectively.]

The drug microspheres of the present invention may be administered as prepared above or may be compounded in a pharmaceutical preparation in which such drug microspheres comprise the active ingredient or one of a plurality of active ingredients, or may be mixed with microspheres containing other drugs. Drug-containing gelatin microspheres may be mixed with placebo gelatin microspheres containing no drug to achieve blends with lower concentration of drug per unit volume or weight.

Suitable pharmaceutical preparations may, for example, take the form of ointments, gels, pastes, creams, sprays (including aerosols), lotions, powders, suspensions, solutions and emulsions of the active ingredient in suitable excipients. Examples of suitable excipients include pharmaceutically acceptable fillers and extenders, binding agents, moisturizing agents, agents for retarding dissolution, disintegrating agents, resorption accelerators, surface active agents, adsorptive carriers, and lubricants. It is understood that the excipient(s) must be chosen to preserve the integrity and activity of the drug microspheres and to be compatible with the selected route of administration.

The pharmaceutical preparations which are powders and sprays can, for example, contain appropriate diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are ointments, pastes, creams and gels can, for example, contain appropriate diluents, e.g. animal and vegetable fats, waxes, paraffins, starch, tragacanth, cellulose derivatives, polyethylene glycols, silicones, bentonites, silicic acid, talc and zinc oxide or mixtures thereof.

The pharmaceutical compositions which are solutions and emulsions can, for example, contain appropriate diluents and emulsifiers known to those in the art, e.g., ethyl alcohol, isopropyl alcohol, ethyl carbonate, ethyl acetate, benzyl alcohol, benzyl benzoate, propylene glycol, 1,3-butylene glycol, dimethylformamide, oils (e.g. ground nut oil), glycerol, tetrahydrofurfuryl alcohol, polyethylene glycols and fatty acid esters of sorbital or mixtures thereof.

The pharmaceutical preparations which are suspensions can contain appropriate diluents (e.g. ethyl alcohol, propylene glycol), surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

The pharmaceutical preparations of the present invention can also contain coloring agents and preservatives as well as perfumes. The pharmaceutical preparations of the present invention contain from 0.1 to 99.5% by weight, preferably from 0.5 to 95% by weight, of the drug-containing microspheres in the total composition.

The production of the above pharmaceutical compositions is carried out by suitable methods well-known to those in the art.

There are a number of viruses, e.g. rhinovirus and adenovirus, which infect warm-blooded animals via the mucosal surfaces. Antiviral agents suitable for treatment of such infections are known but it is desired to provide formulations for enhanced delivery to such mucosal surfaces, particularly to the nasal passages which are one of the primary routes of infection for such viruses.

As the major routes of infection by rhinovirus are the mucosal surfaces of the nose and eyes, it is desired to protect such mucosal surfaces with topical application of appropriate antirhinoviral agents.

Accordingly, it is desirable to have formulations of human major rhinovirus receptor (ICAM-1) or fragments thereof which are capable of residing in the nasal passages for extended periods of time to effect protection against rhinoviral infection in a safe and cost-effective manner.

The gelatin microspheres of the present invention are particularly suitable for intranasal administration. By "intranasally" and "intranasal administration" is meant administration to the nasal cavity in a form intended to remain in the nose, including dry powders, nasal drops, nasal spray, and creams, gels, or other formulations suitable for topical application to the nasal cavity. However, the pharmaceutical gelatin/drug microspheres of the present invention may also be formulated for topical administration, e.g. as creams, lotions, salves, ointments, etc., for topical administration to e.g. to the eye, mouth, ear, skin. Oral formulations may also include troches and mucoadhesive buccal tablets, etc.

The invention will be described in further detail in connection with the following examples, which are directed to administration of antirhinoviral agents, specifically ICAM-1 and fragments thereof, but the gelatin/drug microspheres of the present invention are also suitable for topical administration of other water-soluble pharmaceutical chemical and biological agents, e.g. small chemicals such as antibiotics; proteins, peptides, and polypeptides (e.g., vaccines, antigens, antibodies, lymphokines, and fragments of any of the foregoing); nucleotides (e.g. genes, DNA, RNA, and fragments of any of the foregoing); carbohydrates; and antiviral agents such as Enviroxine, Pirodavir, interferon-alpha, sialidase inhibitors, acyclovir, adenosine, arabinoside, interferon and interferon-inducing agents. The invention can be further understood upon consideration of the following examples. As used hereinabove and below unless expressly stated to the contrary, all temperatures and temperature ranges refer to the centigrade system; the term percent or (%) refers to weight percent; and the term mole and moles refer to gram moles.

EXAMPLES

Example 1

Production of tICAM(453)

Rhinoviruses are members of the picornavirus family and are responsible for 50% of colds in humans over the course of one year. During peak season (mid-September to mid-October) however, rhinoviruses account for up to 75% of all colds. Approximately 90% of all rhinoviruses bind to a major human rhinovirus receptor (HRR). An antiviral agent comprising the human major rhinovirus receptor or fragments thereof is an effective inhibitor of rhinoviral infection of susceptible cells. The human major rhinovirus receptor is the same as the protein known as intercellular adhesion molecule-1 (ICAM-1), with the exception of a G>A at nucleotide 1462, resulting in the amino acid substitution Glu>Lys at amino acid position 442. ICAM-1 is a glycoprotein with a molecular weight of 45–50 kD (excluding carbohydrate) and 8 potential sites for N-linked carbohydrate attachment; the glycosylated protein has a molecular weight of 82–88 kD. ICAM-1 has 507 amino acids and consists of a cytoplasmic domain, a transmembrane domain, and five extracellular immunoglobulin-like domains (amino acids 1–88, 89–185, 186–284, 285–385, and 386–453). The presently preferred embodiment for antiviral purposes is a fragment consisting of the first 453 amino acids of the full HRR sequence, which retains rhinovirus binding activity.

Recombinant tICAM(453) was purified from fermentation fluid of continuous cell culture of Chinese hamster ovary (CHO) cells containing cDNA coding for tICAM(453) maintained by continuous perfusion in a customized medium free of all plasma-derived components. By "tICAM (453)" is meant the first 453 amino acids (domains 1–5) of ICAM-1. The sequence for ICAM-1 is known to those skilled in the art, as are methods of preparing the cDNA coding for tICAM(453). See, e.g,, Staunton, D. E., S. D. Marlin, C. Stratowa, M. L. Dustin, and T. A. Springer, "Primary Structure of ICAM-1 Demonstrates Interaction Between Members of the Immunoglobulin and Integrin Supergene Families", Cell 52:925–933 (1988); European Patent Application Pulbication No. 362,531.tICAM(453) obtained from clarified and concentrated fermentation fluid was purified by hydrophobic chromatography, metal ion chromatography, precipitation at low pH, filtration, anion exchange chromatography, hydroxyapatite adsorption, size exclusion chromatography, and a second HAP adsorption step. Viral inactivation was accomplished via low pH precipitation (demonstrated to reduce MuLV and Reovirus titers by 36 and 22 logs, respectively), and by pasteurization (shown to reduce the reference virus titers by an additional 5 logs). The tICAM(453)-containing solution was sterilized by filtration to yield the liquid drug substance, which was stored at −35° C. until formulated into a gelatin-based microsphere powder. Some lots were lyophilized in phosphate-buffered saline (PBS, or 0.15 M NaCl, 0.01 M $Na_2HPO_4$, adjusted to pH 7.0) and reconstituted before use. tICAM(453) was concentrated to >50 g/L and diafiltered into a low-ionic-strength 10 mM histidine buffer, pH 7.0.

Example 2

Process for Production of Gelatin Microspheres
A) Materials
 tICAM(453): tICAM(453) was made as in Example 1.
 Albumin: 25% albumin (human) USP (Bayer Corporation, Elkhart, Ind.)
 Grades of Gelatin: Acid-type gelatin, extracted from porcine skin, was obtained from Hormel Foods (Austin, Minn.). Gelatin is normally graded by its Bloom strength, a measure of gel strength under defined conditions (see, e.g., U.S. Pat. No. 1,540,979). These studies were conducted with gelatin with Bloom strengths of 225 (Hormel grade P-7), 250 (grade P-8) and 275 (grade P-9).

Oils: A variety of oils was used. Food-grade corn oil was obtained from a grocery store (e.g. Mazola®, CPC International, Englewood Cliffs, N.J.). Pharmaceutical or NF grade was supplied by Ruger Chemical (Irvington, N.J.). Soybean oil was either food-grade or NF grade from Ruger Chemical.

Surfactants: Span 80® (sorbitan monooleate), Span 85® (trioleate), and Arlacel 186™ (glyceryl monooleate) were supplied by ICI Americas (Wilmington, Del.). Pluronic L-1011™ was from BASF (Mt. Olive, N.J.). Lecithin was supplied by Central Soya (Ft. Wayne, Ind.).

Solvents: Acetone and n-heptane were reagent grade, purchased from J T Baker (Phillipsburg, N.J.), EMScience (Gibbstown, N.J.), and Mallinkrodt (Chesterfield, Mo.).

B) Methods:

As the supply of tICAM(453) was limited, this resource was conserved by carrying out range-finding studies on a small scale first without tICAM(453) present, then evaluating the effects of adding tICAM(453) on the process, and finally scaling up the resulting process.

An emulsion volume of 200 mL was selected for these range-finding experiments. This scale allowed the conduct of multiple experiments per day while providing enough material from each experiment for characterization. The outcome of each experiment was evaluated first by a visual examination of the flow properties of the resulting powder. Sticky or highly aggregated material was rejected without further analysis. Material acceptable by visual inspection was analyzed for particle size distribution by laser light scattering.

Once a process at the 200-mL scale (8–10 g dry-weight basis) had been defined, tICAM(453) was included in order to assess its effect on the process and to evaluate the effect of the process on molecular integrity and biological activity.

Finally, the process established in the range-finding experiments was scaled up to the 150-g level to establish commercial utility.

C) General Scheme of Process:

Range-finding experiments were conducted by emulsifying a total volume of 200 mL in a 400-mL beaker (7.3 cm diameter). Either a 1.5" radial-flow impeller (item R100, Lightnin Equipment, Milwaukee, Wis.) or a 2" high-efficiency axial-flow impeller (item A310) was used. The gelatin solution was added to the oil phase while stirring in initial experiments at 700 rpm. After 10 min, the stirring speed was then lowered to 400 rpm. The designs of the impellers is shown in FIG. 1. In other experiments, the stirring rate was held constant.

The initial temperature of emulsification was at least 45° C., and cooling took place by natural convection. Washing was carried out using two 100-mL washes with heptane, followed by two 100-mL washes with acetone. For each wash, the resulting suspension was either stirred by hand or by using a motor-driven mixer. The solids were allowed to settle after each wash by gravity, and the supernatant removed by decantation. The final powder was collected by vacuum filtration on a Buechner funnel, using #3 Whatman (Fairfield, N.J.) filter paper. It was dried overnight under vacuum at 34–40° C.

D) Powder Characterization:

The suitability of the powder was evaluated in stages. Initial evaluation required that the powder be free-flowing, without stickiness attributable to residual oil. Any lumps were removed by passing the powder through a 60- or 70-mesh sieve. Because the goal was to have a powder falling into the size range 10–100 μm, and preferably 20–80 μm, most of the powder should pass easily through either of these sieves, which have cut-off diameters of 250 and 212 μm, respectively.

E) Scale Down and Scale Up Studies:

The range-finding experiments in section C above served to determine a suitable composition for the emulsion being prepared, i.e., oil and surfactant choice, concentrations, etc. Process reproducibility was examined at the 2.5-g scale (50 mL emulsion). This was considered the smallest scale at which the process could be carried out without altering critical parameters.

F) Calculation of tICAM(453) and Albumin Loading:

Theoretical loading of tICAM(453) and albumin were calculated on the following basis:

i) The moisture content of the gelatin raw material and of the final product were assumed to be similar. Thus, moisture content could be ignored.

ii) Only the polypeptide portion of the tICAM(453) molecule (and not the carbohydrate portion) was taken into account.

These assumptions, when used consistently in calculating loading, pose no difficulties. These assumptions do not apply and must be corrected for when calculating the dry-weight powder yield.

The theoretical loading is given by:

$$f_i = \frac{c_i m_i}{[c_i + c_b]m_i + G_g m_g \rho_i}$$

This expression is based on a mass balance for the preparation of a gelatin solution containing tICAM(453) (or albumin). In the expression, $f_i$ is the mass fraction (or loading) of ICAM(453) (or albumin), $c_i$ is the concentration, in g/L, of tICAM(453) (or albumin) in the original solution, $\rho_i$ is the density of the tICAM(453) (or albumin) solution, in g/L, and $m_i$ is the mass of the tICAM(453) (or albumin) solution used. The buffer salt concentration for the tICAM(453) (or albumin) solution is given by $c_b$ (in g/L); this can be significant if the tICAM(453) (or albumin) concentration is low and the buffer is phosphate-buffered saline. For a low-salt buffer, the correction given by $c_b$ is small. The total mass of gelatin used is $G_g m_g$ for the case where a gelatin solution is mixed with an tICAM(453) (or albumin) solution. $m_g$ represents the mass of gelatin solution, and $G_g$ the mass fraction (g/g) of gelatin before adding the tICAM(453) (or albumin). The solution densities were measured and found to be 1020 g/L for tICAM(453) at 50 g/L and 1070 g/L for albumin at 250 g/L.

G) Results:

Surfactant choice:

Five oil-soluble surfactants were tested, having a variety of chemical compositions. These were Span 80 and 85, Pluronic L-1011, Arlacel 186, and soybean lecithin. Each of these was tested in corn oil at the 1% level in the 200-mL model system under the conditions shown in Table I:

TABLE I

Effect of Surfactant Choice on Particle Size Distribution
In common: Porcine 250-bloom type A gelatin 20% (w/w) in water, emulsified in corn oil

| Surfactant | Result | D[4,3], μm |
|---|---|---|
| 1:4 gelatin-oil ratio: A310 impeller, at 700/400 rpm (start/end) | | |
| Span 80 | 89% through 60 mesh | 112 |
| Arlacel 186 | coarse powder | n.d. |
| 1:3 gelatin-oil ratio, 650 rpm | | |
| Span 80 | 99% through 70-mesh | 57 |
| Span 85 | 0% through 70-mesh | n.d. |
| Lecithin | oily powder; difficult to wash | n.d. |

D[4,3] = mean volume particle diameter; the volume particle diameter is the diameter of a sphere having the same volume as the given particle These experiments showed that Span 80 and L-1011 were superior to the other surfactants (data for L-1011 not shown). Given that L-1011 is not available in a compendial (USP or NF) grade, Span 80 was selected for use in further studies. Span 80 concentration:

Surfactant concentration was investigated at 0.1, 1, and 2% (w/v), and at gelatin:oil ratios of 1:2 to 1:4 (Table II) at 200 mL volume scale:

TABLE II

Effect of Span 80 Concentration

Conditions: Porcine 250 Bloom type A gelatin at 20% (w/w) in water; emulsified in corn oil
volume ratio 1:4; 2" A310 impeller at 700/400 rpm (start/end)

| Concentration | % through 60-mesh sieve | D[4,3], μm |
|---|---|---|
| 0.1% | n.d.* | 202 |
| 1.0% | 89% | 112 |
|  | 93% | 113 |
| 2.0% | n.d. | 65 |
|  | 93% | 116 | volume ratio 1:4 (cont'd); 1.5" R100 impeller at 700/400 rpm (start/end)

| Conc. | % through 60-mesh sieve | D[4,3], μm |
|---|---|---|
| 0.1% | 82% | 196 |
| 1.0% | n.d. | 87 |
|  | 90% | 131 |
| 2.0% | n.d. | 117 |

1:3 volume ratio; 1.5" R100 impeller at 650 rpm

| Conc. | % through 70-mesh sieve | D[4,3], μm |
|---|---|---|
| 0.1% | 0% | n.d. |
| 1.0% | 98% | 63 |
| 2.0% | 92% | 103 |

1:2 volume ratio; 1.5" R100 impeller at 700/400 rpm (start/end)

| Conc. | % through sieve | D[4,3], μm |
|---|---|---|
| 0.1% | sticky | n.d. |
| 1.0% | 93% (60-mesh) | 130 |
|  | n.d. | 120 |
| 2.0% | 94% (70-mesh) | 133 |

1:2 volume ratio (cont'd); 2" A310 impeller at 700/400 rpm (start/end)

TABLE II-continued

Effect of Span 80 Concentration

| Conc. | % through 70-mesh sieve | D[4,3], μm |
|---|---|---|
| 0.1% | sticky | |
| 1.0% | n.d. | 129 μm |
| | 99% | 130 |
| | 93% | 180 |
| 2.0% | 98% | 116 |

*n.d. = not determined

The table shows that at the 1:4 ratio, particles decreased in size with increasing concentration of Span 80 up to and including 1%, but that increasing the surfactant concentration beyond 1% had little effect. When the amount of gelatin was increased relative to the oil, representing more difficult emulsification conditions, this effect was even more marked. Based on these experiments, 1% Span 80 was used in all further investigations.

Gelatin-Oil ratio:

This ratio was defined as the ratio, by volume, of a solution of 20% (w/w) porcine 25 Bloom type A gelatin: corn oil containing 1% Span 80. Ratios of 1:4 to 1:1 were examined. Higher ratios are preferred because at a given scale, oil and solvent consumption and processing volume are reduced. At the same time, a higher proportion of gelatin solution in the emulsion increases the likelihood that droplets or beads collide with each other, resulting in increased incidence of coalescence or aggregation.

Indeed, multiple attempts to use a 1:1 ratio failed, for reasons including inversion of the emulsion, difficulty in washing out the oil, and unacceptably large (>200 μm) microspheres.

Microspheres of the desired size were obtained at a ratio of 1:3 in multiple runs at varying scales. The difference between ratios of 1:3 and 1:2 is slight: at the 200-mL scale, 5 runs at a ratio of 1:3 led to sizes of 62.8±14.6 μm, while a single run at 1:2 led to 77.0-μm microspheres (FIG. 2). Mixing was with a 1.5" R100 (radial flow) impeller, used at 600/700 RPM (start/end).

Oil Type:

Corn and soybean oils were both evaluated over a period of time. The results of these comparisons under two different conditions are shown in Table III:

TABLE III

Soybean vs. Corn Oil in Paired Experiments

| oil type | % through 70-mesh sieve | D[4,3], μm |
|---|---|---|
| 1:2 volume ratio;2" A310 impeller at 700/400 rpm (start/end) | | |
| corn | 99 | 129.9 |
| soybean | 96 | 148.8 |
| 1:3 volume ratio;1.5" R100 impeller, 650–700 rpm | | |
| corn | 99 | 53 |
| soybean | 100 | 53 |
| corn | 98 | 74 |
| corn | 89 | 80 |
| soybean | 98 | 74 |
| soybean | 92 | n.d. |
| soybean | 94 | n.d. |
| soybean | 99 | 69 |
| soybean | 98 | 69 |
| soybean | 93 | 81 |

TABLE III-continued

Soybean vs. Corn Oil in Paired Experiments

| oil type | % through 70-mesh sieve | D[4,3], μm |
|---|---|---|
| soybean | 93 | 90 |
| corn | 99 | 82 |
| corn | 99 | 64 |
| corn | 97 | 67 |
| soybean | 98 | 55 |

The table suggests that there is no profound difference in the results between normally-refined corn and soybean oils, as might be expected from their similar viscosities.

Processing Conditions, Stirring Speed, Impeller Type, and Washing Method:

Selection of appropriate surfactant, oil type, etc. can be applied to larger scales. Appropriate mixing conditions during emulsification are more scale-dependent. Nevertheless, the above experiments illustrate the relative importance of these variables. As indicated in Tables II and III, the choice of impeller had little bearing on the final particle diameter at the 200-mL scale. This may be because the two impellers used at this scale were almost as large as the vessel itself: the ratios of impeller to vessel diameter were 0.52 and 0.70.

The mixing and washing conditions at the 200 mL scale had more of a bearing on the final size. Initially, washing was carried out by occasionally stirring the emulsion in solvent with a spatula. This was changed to continuous mixing using a propeller mixer. At the same time, the procedure for emulsification was changed. Instead of stirring for 700 rpm for 10 min, and then at 400 rpm, the stirring speed was kept constant. In Table IV, the results of these changes are summarized:

TABLE IV

The Effect of Stirring Speed (Emulsion) and Mixing Method (Washing) Conditions: 1:3 volume ratio of 20% (w/w) Porcine 250 Bloom type A gelatin inwater:1% Span 80 in corn oil, 200–240 mL scale

| Speed, rpm (start/end) | | stirred wash? | D[4,3], μm |
|---|---|---|---|
| 2" A310 impeller | | | |
| 700/400 | | No | 84 |
| | | No | 162 |
| 550/550 | | Yes | 55 |

| Speed, rpm (start/end) | | stirred wash? | D[4,3], μm |
|---|---|---|---|
| 1.5" R100 impeller | | | |
| 700/400 | 13 runs | No | 109 ± 34 |
| | 2 runs | Yes | 63 ± 4 |
| all speeds | 27 runs | Yes | 67 ± 10 |

The table shows that before implementing these changes, particles were large and varied in size from batch to batch. It also shows that mixing conditions during emulsion cooling do influence the final diameter.

Two runs were performed using two mixing speeds, but with continuous stirring during the washing phase. In these two runs, there was a reduction in both mean volume particle diameter and variability as measured by the between-run standard deviation.

Numerous additional runs were carried out where both changes were implemented. In these runs (25) there was also a reduction in both mean volume particle diameter and standard deviation relative to the initial preparation conditions, using either the A310 or R100 impellers.

H) Summary:

The results of the experiments described above allowed definition of a "standard process" before investigating the effects of incorporating drug. The choice of surfactant was clear—Span 80—and the concentration was set at 1% (w/v) because higher concentrations offered little additional advantage. Corn and soybean oils were equivalent in many respects: the particle size distribution did not differ significantly, both are available in compendial grade, and both are commonly used as pharmaceutical excipients. Corn oil was chosen because its cost is lower than soybean oil.

The gelatin solution was set at 20% (w/w) solids. It is difficult to remove entrained air or pour gelatin solutions at higher concentrations. Lower concentrations appeared to offer little advantage, and would require extra oil and solvent per gram of final product.

The volume ratio of gelatin to oil was set to 1:3. It is desirable to use as little oil as possible. As described above, reducing the oil to 1:2 made it more difficult to obtain the desired particle-size distribution.

Rapid cooling or longer stirring reduced the mean volume particle diameter. Gelation of gelatin solutions is a kinetic phenomenon, so that gel strength is a function of both time and temperature.

Example 3

Incorporation of tICAM(453)

tICAM(453) was incorporated into the gelatin microspheres made by the process of Example 2 to evaluate the effect of the protein on particle size; determine protein loading; and evaluate the effect of processing conditions on bioactivity. Emulsification conditions were 1:3 volume ratio of 20% porcine 250 Bloom type A gelatin in water (w/w):1% Span 80 in corn oil.

Initial experiments were conducted as shown in Table V:

TABLE V tICAM(453) Parameters at the 240-mL Scale

| | | |
|---|---|---|
| D[4,3] | 72 μm | |
| total solids: | 20% | |
| tICAM(453) bioactivity: | starting material: | 0.43 μg/mL |
| | released from formulation: | 0.43 |
| | (control) | 0.29 |
| Theoretical loading: | 8.9% | |
| Final loading: | 7.8% (87% of theoretical) | |
| Control lots (2): | D[4,3] = 53, 60 μm | |

In the top part of the table, the results of a run incorporating tICAM(453) are presented. In the lower part are the results of two control runs. The tICAM(453)-loaded material had a slightly higher mean volume particle diameter than the controls. tICAM(453) released from the formulation had bioactivity identical to the starting material. The measured loading was 7.8%; this was 87% of the loading expected based on the composition of the initial gelatin solution.

Example 4

Process Reproducibility

Process reproducibility was investigated in several runs at the 50–60-mL scale (2.5–3 g) under the same conditions as in Example 3, as shown in Table VI:

TABLE VI

Process Reproducibility at the 50–60-mL (2.5–3-g) Scale

| Run #: | 1 | 2 | 3 | 4 | 5 |
|---|---|---|---|---|---|
| Scale | 2.5 g | 2.5 g | 2.5 g | 3 g | 3 g |
| Target loading | 11.5% | 10.9% | 11.7% | 14.0% | 13.8% |
| Actual loading | 10.0% | 9.9% | 10.3% | 12.1% | 11.7% |
| % of expected | 87% | 91% | 88% | 86% | 85% |
| % 140–635 mesh | 88% | 97% | 95% | — | — |
| % <70 mesh | 98% | 100% | 100% | 97% | 96% |
| tICAM(453) yield (%) | 74% | 81% | 83% | 86% | 78% |
| Solids yield (%) | 97% | 92% | 94% | 99% | 96% |
| Light scattering: | | | | | |
| D[4,3], μm | 61 | 53 | 49 | 95 | 61 |
| % of particles with <9.5 μm volume particle diameter | 0% | 0.4% | 0% | 0.1% | 0.2% |
| % of particles with >101 μm volume particle diameter | 7% | 2% | 1% | 34% | 7.6% |
| Notes | | | | corn oil | soybean oil |

Plaque assays were performed according to the method of Greve et al., J. Virol. 65:6015-23 (1991) and results are shown below:

| tICAM(453) (starting material) | tICAM(453)/ gelatin solution | Released tICAM(453) | control |
|---|---|---|---|
| 0.26 | 0.39 | 0.23 | 0.30 |
| 0.48 | 0.68 | 0.34 | 0.39 |
| 0.41 | 0.42 | 0.46 | 0.25 |
| 0.32 | 0.32 | 0.34 | 0.34 |

Potency results are expressed as a concentration in μg/mL necessary to inhibit viral infection of susceptible cells. Thus, higher values reflect lower potency.

These experiments had several purposes: (1) to show that the formulation process, of Example 3, could be carried out reproducibly, (2) to demonstrate that tICAM(453) would remain active once released from the formulation, and (3) to determine an appropriate initial loading required to obtain 10% tICAM(453) in the final formulation.

Initially, two runs were performed to establish what the final loading of tICAM(453), expressed as a percentage of the initial, theoretical loading. These are summarized in Table VI, runs 4 and 5. These two runs, plus the result shown in Table V together showed that the tICAM(453) loading is between 85 and 87% of that expected from the gelatin solution. Therefore for a 10% loading the initial tICAM (453) content should be 11.8%.

Runs 1,2, and 3 in Table VI were carried out in order to show consistent tICAM(453) loading, particle size distribution, and yield. In addition, the bioactivity of the tICAM(453) released from the powder was measured and found to be comparable to the starting material.

Interestingly, the tICAM(453) yield was <100%. The nephelometric assay for tICAM(453) detects both active and inactive tICAM(453), so the loss of material is not assay-related. The most likely point at which tICAM(453) is lost is in the initial acetone wash. If all of the water present is extracted into the acetone phase, it will contain 17% water. This may be enough to dissolve tICAM(453) and perhaps gelatin as well.

The biological activity of the tICAM(453) is not affected by the process conditions.

Example 5

Process Scale-Up

Parameters for the scale-up of the process were investigated. In initial larger-scale experiments, it was assumed that only the mixing conditions need be modified, and that other process parameters could be kept constant.

A scale of 150 g was selected as the target. At this scale (3 L emulsion), cooling under ambient conditions was too slow, therefore the mixing vessel was immersed in a refrigerated water bath at an initial temperature of 50–55° C. The gelatin solution was added to the warm oil, and the refrigeration unit was immediately turned on. It took approximately 70 min before the emulsion reached its final temperature of 10° C.

Factors influencing particle size, where the emulsion composition was held constant, were expected to be:

i) impeller size and type ii) impeller position iii) tank dimensions iv) temperature profile with time v) presence of tICAM(453) (keeping solids at 20%).

It is important to apply the necessary level of agitation without entrainment of air. The stirring speed is limited by the formation of a vortex in the emulsion. Because vortex formation was undesirable, particles of the desired diameter could not be obtained while stirring at constant speed, even when the impeller was placed in the optimal position. As the emulsion cooled, the emulsion viscosity increased, and it was possible to increase the stirring speed during the cooling process without increasing vortexing. When this was done, particles of the desired size were achieved.

Therefore it is critical that the stirring accomplish two things: first, to provide sufficient shear to break up the gelatin solution into sufficiently small droplets, and second, to provide sufficient fluid flow so that no stagnant zones form near the walls. It appeared that the latter consideration was more important, given that as the emulsion cooled, it seemed to become shear-thinning, particularly at a gelatin-oil ratio of 1:3. Under that circumstance, a small impeller could provide a high degree of shear and flow only in a zone surrounding the impeller.

Ordinarily, if there is a problem with vortexing, it can be solved by the addition of baffles. Indeed, baffles did allow an increase in mixing speed over the unbaffled configuration. At the same time, the gap between the baffle and the tank wall was only ⅛" (3 mm), potentially allowing a build-up of cool, slowly moving material to accumulate. If baffling is used care must be taken to avoid this problem.

Two separate approaches to scale-up were used, each of which had its advantages. In the first approach, the mixing shaft was positioned along the axis of the beaker. The impeller itself was as large as would feasibly fit into the vessel, and was positioned close to the bottom. In this configuration, a large, deep vortex formed, exposing the center portion of the impeller so that only the tips of the blades entered the solution. The emulsion was cooled by packing ice bags around the vessel. With this configuration, experiments with and without tICAM(453) were conducted at the 3-L scale. The results are shown in Table VII:

TABLE VII

Batches at the 150-g Scale: Centered Impeller
1:3 volume ratio of 20% (w/w) porcine 250-Bloom type A gelatin in water: 1% Span 80 in corn oil
emulsion volume 3 L; impeller: 3.5" (8.9-cm) marine propeller (10° pitch)

| Mixing speed (rpm) | tICAM(453) -loaded? | D[4,3], $\mu$m |
|---|---|---|
| 760 | No | 67 |
| 850 | No | 56 |
| 850 | No | 55 |
| 850 | Yes | 49 |

The table shows that a 3½" (8.9 cm) marine propeller with shallow pitch (~10°) served, when driven at 850 rpm, to create microspheres with a mean diameter of 50 –70 $\mu$m. Incorporation of tICAM(453) at 10% did not have a significant effect on the particle size.

This procedure did have some disadvantages. The propeller caused splashing of the oil phase, particularly during the initial phase of the run, and air could potentially be entrained into the emulsion, causing tICAM(453) denaturation or foaming, which would interfere with the with the subsequent washing steps. Therefore an approach in which vortexing and entrainment of air were minimized was also pursued.

At the larger scales (120 g and up), the beneficial rate of cooling adds to the complexity of scale-up. Because cooling is carried out from the vessel walls, there is a boundary layer of cooler and therefore more viscous emulsion near the wall of the tank. This layer is kept thin by mixing action. At higher cooling rates, the thermal (and thus hydrodynamic) boundary layer becomes thicker, and more intensive mixing is necessary to offset this effect.

With the lower cooling rate at larger scale, it was unclear whether any extra stirring time to allow hardening is necessary. To avoid the possibility of problems a 1-hr hold step was included in the process.

Studies were carried out in order to determine suitable impellers for evaluation. A 3-L emulsion containing 750 mL gelatin solution was held at 50° C. in a beaker with a diameter of 20.3 cm. The impellers listed below were tested in as many as three different positions: vertically mounted and centered, vertically-mounted and off-center, and mounted at an angle of 10–15° from vertical in the off-center position (see FIG. 3).

The maximum speed that each impeller could be turned was checked, and the mixing behavior examined qualitatively at that speed. The results are shown in Table VIII:

TABLE VIII

Mixing Studies at the 3-L Scale

| Impeller | Type | Size (in) | Mounting | Max Speed (rpm) | Tip Speed (in/min) | Notes |
|---|---|---|---|---|---|---|
| R100 | radial flow | 2 | vertical, off-center | 900 | 5700 | |
| | | | angled, off-center | 940 | 5900 | improved pumping |
| | | | vertical, centered | 770 | 4800 | poor flow at walls |
| A200 | axial flow (4 blades, 45° pitch) | 2 | vertical, off-center | 1000 | 6300 | eddies, one deep vortex |
| | | | angled, off-center | 1000 | 6300 | same |
| A310 | high efficiency axial flow | 2.5 | angled, off-center | 1160 | 9100 | narrow vortex, leading to air entrainment and loss of mixing. Dead spots. |
| Marine | 45° pitch | 3 | angled, off-center | 490 | 4600 | |
| Marine | 10° pitch | 3.5 | vertical, off center | 630 | 6900 | poor vertical mixing, stagnation at walls |
| | | | angled, off center | 660 | 7300 | same |

Direct comparisons of the different impeller designs was difficult because the diameters of the impellers available were not all the same. Nevertheless, it appeared that the most attractive design was the radial-flow impeller, and that the impeller should be positioned off-center.

It was decided to position the impeller at an angle in the "upper-left" quadrant of the mixing vessel, as shown in FIG. 3. This position minimizes the formation of a vortex. A number of experiments are summarized in Table IX, arranged in order of increasing scale, but incorporating a variety of impellers, vessel diameters, and mixing speeds:

TABLE IX

Scale-Up Studies

| Scale (dry basis), g | Volume (L) | Vessel dia. (cm) | impeller | mixing speed, rpm | drying method | D[4,3], μm | notes |
|---|---|---|---|---|---|---|---|
| 150 | 3.0 | 20.3 | R100 (2") | 1000 | | 100* | impeller at constant speed |
| 150 | 3.0 | 20.3 | R100 (2") | | | 126* | gradually increased speed to 1600 rpm |
| 150 | 3.0 | 17.1 | R100 (3") | 400–640 | | 50* | final emulsion kept cool |
| 180 | 3.6 | 20.5 | A310 (3.8") | 440 | o/n vacuum | n.d. | 52% <140 mesh when sieved. Propeller incorrectly positioned |
| 300 | 6.0 | 20.3 | A310 (3.8") | 500–550 | ambient | 91 | poor washing |
| 300 | 6.0 | 20.3 | A310 (3.8") | 520 | fluidized bed | 74 | stirrer speed increased to 640 rpm when T = 42° C. Result close to target. | o/n = overnight;
n.d. = not determined;
*before drying

Table IX shows that the particles obtained at the 300-g scale were unacceptably large. Exhaustive experimentation was not performed because one specific configuration was successful at the 150-g scale: a 3" (7.6 cm) radial-flow (R100) impeller mounted in a 4.5-L (17.1 cm diameter) beaker.

Minor adjustment of conditions may be needed to achieve the desired particle size distribution; these are within the purview of those skilled in the art. For example, as increasingly larger vessels of 7.3 cm to 20 cm diameter were used, the impeller-to-tank diameter ratio actually increased. This may be related to thixotropy of the cooled emulsion, which tends to limit the zone of active fluid motion to a region around the impeller. At substantially higher scales (e.g., >1000 g, where the emulsion volume will be >25 L), the above approach may become impractical and other methods must be substituted to intensify the level of mixing. One alternative is a semi-batch form of operation, where mixing is done in-line. Modest changes in scale would be accomplished via changes in the total processing time.

Example 6

Adjustments to Avoid Precipitation of Drug

If the drug to be delivered is a protein having an isoelectric point such that it tends to precipitate during the process of Examples 3 and 5, adjustments can readily be made to avoid such precipitation. For example, albumin precipitates when added to warm gelatin solution, because gelatin solutions at 20 wt % have pH values of approximately 5, close to the isoelectric point of albumin. Precipitation was avoided by adjusting the pH of the gelatin solution to 6.0–6.1 or by dissolving the gelatin initially in 0.019 M NaOH.

Similar adjustments to avoid such problems with other drugs are expected to occur to those skilled in the art.

Example 7

General Process for Preparation of Pharmaceutical Grade tICAM(453)/gelatin Microspheres The gelatin/tICAM(453) microspheres are prepared by a process that begins by mixing a solution of tICAM(453) and gelatin in corn oil to form a water-in-oil emulsion. This emulsification process uses corn oil, gelatin, Span 80, water for injection, and tICAM(453) in L-histidine buffer as the raw materials. The wet gelatin beads are subsequently washed with acetone to remove the oil and surfactant, and to dehydrate the gelatin beads into a dry microsphere powder. Residual acetone is removed and the final moisture content is fixed by fluidizing a bed of the microspheres with an air stream of controlled humidity.

Table X lists the quantitative composition of tICAM(453)/gelatin microspheres and placebo (gelatin microspheres only) bulk powder preparations prepared by this process.

TABLE X

Unit formula listing components for placebo and tICAM(453)/gelatin microsphere bulk powder preparation.

|  | Placebo | tICAM(453)/ gelatin microsphere (10% load) |
| --- | --- | --- |
| Gelatin | 150 g | 104.7 g |
| L-Histidine |  | 0.4 g |
| tICAM(453) |  | 14.9 g |
| Batch size (total of above) | 150 g | 120 g |
| Water for injection* | 600 g | 480 g |
| Total aqueous volume | 750 mL | 600 mL |
| Corn oil** |  |  |
| Weight | 2070 g | 2208 g |
| Volume | 2250 mL | 2400 mL |
| Span 80** | 22.5 g | 24.0 g |
| Acetone** | approx. 15 L | approx. 15 L |

*including that added along with ICAM. Partially removed during processing.
**Removed during processing. Span 80 and corn oil are reduced to respective levels of ≦0.14 and ≦0.3 mg/g of gelatin microsphere powder. Acetone at the end of the process complies to a limit of ≦250 ppm.

Example 8

General Process for Preparation of Pharmaceutical Grade tICAM(453)/gelatin Microspheres The following is a standard general procedure used repeatedly for the production of tICAM(453)/gelatin microspheres:

1. tICAM(453) is concentrated to >50 g/L and diafiltered into a low-ionic strength 10 mM histidine buffer, pH 7.0. The ultrafiltration/diafiltration (UF/DF) is carried out using a model S10Y30 (30,000 MWCO) tangential-flow ultrafiltration cartridge (Amicon, Beverly, Mass.) with at least 7 volumes of the histidine diafiltration buffer.

2. The final UF/DF formulated tICAM(453) bulk is sterile-filtered through a 0.2-micron filter into sterile polyethylene terephthalate copolymer (PETG) bottles and stored at not more than −30° C. Aliquots of the sterile formulated bulk are used to quantitate tICAM(453) content by immunonephelometry, tICAM(453) integrity by SDS-PAGE, bioactivity by the cell-based plaque assay, and microbial load. Immunonephelometry is a method for assaying the concentration of a specific protein in solution based on measurement of the intensity of light scattered from precipitation formed by mixing the protein of interest with antibodies reactive against it. Automated instruments for carrying out this assay are manufactured, for example, by Behring Diagnostics, Inc. (Somerville, N.J.).

3. At the time of formulation, the tICAM(453) is thawed by placing the bottle in a water bath set at not more than 40° C.

4. A solution composition of 104.7 g of gelatin, 14.9 g of tICAM(453) in histidine buffer from step 1, and sufficient water for injection for a total weight of 600 g is prepared in a 1 L glass beaker. This tICAM(453) gelatin solution has a total solids content of 20% (w/w) with tICAM(453) comprising 12.4% of the total solids. The mixture is stirred while covered for not more than 30 minutes in a 50° C. water bath. In a separate 4.5 L stainless steel beaker, 2208 g (2400 mL) of corn oil and 24 g of Span 80 (=1%) are mixed at 200 rpm in a 50° C. water bath for not less than 30 minutes using a 3-inch radial flow impeller attached to a Lightnin® mixer (Lightnin Equipment Co., Milwaukee, Wis.).

5. To generate the water-in-oil emulsion, the speed of the mixer in the oil solution is increased to 300 rpm, and the warm tICAM(453) gelatin solution is gently poured into the oil/surfactant solution over a period of approximately 1 minute. The mixer speed is then increased to 425 rpm to form gelatin-water droplets in the oil/surfactant phase. The water bath set-point is reduced to 10° C. and the emulsion mixed until its temperature reaches 15° C. During this period, the mixer speed is increased at 10-minute intervals to the maximum speed attainable without causing air entrainment. This process cools and solidifies the gelatin-tICAM(453) aqueous droplets into gel beads. Once the emulsion temperature reaches 15° C., the emulsion is mixed for not less than 60 minutes at a mixing speed of not more than 640 rpm. This step hardens and stabilizes the gelatin/tICAM(453) beads.

6. The cooled emulsion is transferred into a 7.6 L stainless steel beaker and the gel beads are subsequently separated from the oil and surfactant by washing the emulsion with acetone. Six washes with acetone remove the oil/surfactant phase of the emulsion and dehydrate the tICAM(453)/gelatin into microspheres of the target particle size.

7. The microspheres are collected on a 3.0-micron Teflon®-type FS filter (Millipore, Bedford, Mass.) in a Buechner funnel set on a filtration flask connected to a vacuum line. The microspheres are dried into a free flowing powder by drawing a vacuum until no further filtrate emerges from the funnel. All the microspheres from the Buechner funnel are transferred to a 60-mesh stainless steel sieve and sieved into a collecting pan. This powder corresponds to one of two sub-batches of the tICAM(453)/gelatin microsphere bulk powder batches that are combined prior to the next manufacturing step. The powder is transferred into a type-III flint glass bottle capped with a Teflon®-lined lid and stored at 2–8° C. until removal of the acetone as set forth in Example 15 below.

tICAM(453)/gelatin microspheres made by this procedure had approximately a 10% tICAM(453) content. Particles made by this procedure are shown in FIG. 5.

Example 9

General Procedure for Preparation of Placebo

The following is a standard general procedure used repeatedly for the production of tICAM(453)/gelatin microspheres:

Placebo gelatin microspheres (no drug loading) are prepared by a procedure which follows steps 4 to 7 of the procedure of Example 8 above, omitting the addition of tICAM(453). The process steps used for manufacturing both tICAM(453)-loaded microspheres and placebo microspheres are identical except that slightly different gelatin:oil ratios are employed in the emulsification processes for tICAM(453)-loaded microspheres compared with the placebo gelatin microspheres in order to obtain similar particle sizes. This is achieved by changing the gelatin:oil ratio from 1:4 (for tICAM(453)-loaded microspheres) to 1:3 (for placebo gelatin microspheres) while keeping the emulsion volume constant for both.

Example 10

General Procedure for Preparation of albumin/gelatin Microspheres

The following is a standard general procedure used repeatedly for the production of albumin/gelatin microspheres:

Albumin/gelatin microspheres are prepared according to the process of Example 8, with the following changes to the preparation of the gelatin solution: A solution of gelatin and albumin is prepared by dissolving 104.8 g of 250-Bloom gelatin in 436.3 g of 0.019 M NaOH at 50° C. 58.7 g of 25% albumin (human) USP (Bayer Corp, Elkhardt, Ind.) is added. This corresponds to a solids concentration of 20% and an albumin loading of 12.3% and leads to an albumin loading of 10% in the final product. The presence of the NaOH in the albumin/gelatin solution is needed to prevent isoelectric precipitation of albumin. The gelatin solution at this concentration would otherwise have a pH of 4–5. This albumin/gelatin solution is emulsified in corn oil and processed as in steps 4–7 of Example 8.

When the powder recovered from two runs prepared according to the above process was combined after the vacuum filtration, and treated by the acetone removal process described in Example 13 and the moisture removal process of Example 14, gelatin microspheres having a mean volume particle diameter of 43 μm, with no detectable particles of volume diameter <10 μm or >100 μm were obtained. The final albumin loading was 10.6% by weight.

Example 11

Adjustments for Particle Size

Comparisons were made between placebo (gelatin only) microspheres prepared by the method of Example 9 and albumin-loaded microspheres prepared by the method of Example 10. Results are shown in Table XI:

TABLE XI

Effect of Albumin on Particle Size
Volume: 3L; 17.3 cm beaker; 1:3 volume ratio gelatin:oil;
20% solids; 3" R100 impeller

| Loading | D[4.3], μm | % > 101 μm |
|---|---|---|
| 0% | 50 | 1.1 |
| 0% | 68 | 9.6 |
| 0% | 64 | 4.8 |
| 10% albumin | 96 | 35 |
| 10% albumin | 118 | 68 |
| 10% albumin | 98 | 40 |

This shows clearly that the presence of albumin increased the mean volume particle diameter.

tICAM(453) also increased the mean volume particle diameter. To study this, experiments were carried out at an intermediate scale, i.e., with an emulsion volume of 800 mL in a 12.5-cm vessel and a 2" R100 impeller (40 g dry weight). At the 800-mL scale (Table XII), and with gelatin:oil ratio of 1:3, albumin loaded microspheres were only slightly larger than placebo microspheres (73 versus 62 μm). At a gelatin:oil ratio of 1:4, albumin-loaded microspheres had a mean volume particle diameter of 57 μm compared to 47 μm for placebo.

TABLE XII

Comparison of Placebo Gelatin Microspheres, Albumin-Loaded Gelatin Microspheres, and tICAM(453)-Loaded Gelatin Microspheres

| loading | volume (mL) | Gelatin-Oil Ratio | D[4,3], μm | % >101 μm | % solids |
|---|---|---|---|---|---|
| placebo | 800 | 1:3 | 62 | 4.6 | 20 |
| albumin | 800 | 1:3 | 73 | 9.0 | 20 |
| tICAM(453) | 800 | 1:3 | 92 | 31 | 20 |
| tICAM(453) | 800 | 1:3 | 165 | 92 | 20 |
| placebo | 800 | 1:4 | 47 | 0.9 | 20 |
| albumin | 800 | 1:4 | 57 | 2.0 | 20 |
| tICAM(453) | 800 | 1:4 | 63 | 4.1 | 20 |
| tICAM(453) | 3000 | 1:4 | 63 | 5.0 | 20 |

However, the mean volume particle diameters of tICAM (453)-loaded microspheres were much larger than the placebo (92 and 165 μm vs. 62 μm, respectively). These experiments showed that tICAM(453) causes an increase in the mean volume particle.

The effect of the loaded protein on particle size was readily minimized by changing the gelatin:oil ratio from 1:3 to 1:4 while keeping the emulsion volume constant. This was first shown at the 800-mL scale (Table XII). At the oil:gelatin ratio 1:4, both albumin and tICAM(453)-loaded microspheres were larger than the placebo microspheres, but more importantly, both the albumin-loaded and tICAM (453)-loaded microspheres exhibited a pharmaceutically acceptable size distribution.

Example 12

Process for Producing tICAM(453)-Loaded Gelatin Microspheres in Larger Batches The process used above in Table XII (3000 mL) was used to prepare larger batches and is further shown below:

| Materials | |
|---|---|
| 250-Bloom gelatin: | 105 g |
| tICAM(453) in histidine buffer | 15 g (12.4% theoretical loading) |
| corn oil ($\rho$ = 0.92) | 2200 g |
| Span 80 | 24 g |

Emulsification

| | |
|---|---|
| Gelatin-tICAM(453) solution weight: | 600 g |
| Beaker diameter | 17.3 cm |
| Impeller: | 76 mm R100 in off-center position shaft 10–15° from vertical |
| Speed: | 400, increased to 640 rpm during cooling |

Temperatures

| | |
|---|---|
| Initial: | 45–50° C. |
| Cooling to 15° C. over ~70 min | |
| Hardening for 1 hr at <15° C. | |

Washing

Seven washes with acetone, each with stirring for 10 min and 10-min settling time.

| Wash volumes: | 1 | 3 L |
|---|---|---|
| | 2–5 | 2 L |
| | 6–7 | 1 L (5 min stirring and settling) |

Filtration in Buechner funnel, using 3.0-µm Millipore Fluoropore filter

Results are shown in Table XIII below:

TABLE XIII

Characterization and Stability of Preclinical Microsphere Formulations

| | ICAM-loaded #1 | | ICAM-loaded #2 | |
|---|---|---|---|---|
| Assay Results | Initial | 3 month 5° C. | Initial | 3 month 5° C. |
| Mean Volume Particle Diameter, µ | 47 | 46 | 46 | 47 |
| % < 10µ | 0 | 0 | 0 | 0 |
| % > 10µ | 0 | 1 | 0 | 1 |
| Moisture, % | 14.9 | 15.4 | 14.5 | 15.7 |
| Residual Acetone, ppm | <150 | | 90 | |
| Loading, % (by immunonephelometry) | 10.5 | 12.1 | 11.1 | 12.4 |
| Potency, µg/ml (by plaque assay) | 0.28 | 0.45 | 0.28 | 0.40 |
| Identity/Integrity (Western blot) | Intact | Intact | Intact | Intact |

Example 13

General Procedure for Removal of Residual Acetone

The following is a standard general procedure used repeatedly for the removal of residual acetone from pharmaceutical compositions comprising gelatin microspheres:

The product of Example 8 (240 g theoretical weight) is charged into a 13-cm Amicon Vantage® S2 column (Amicon, Beverly, Mass.) connected to a sterile air supply and two gas washing bottles. One bottle is immersed in a water bath set at 24° C., and the second bottle is set as a moisture trap. The air is humidified during its passage through the first bottle at a flow rate of 15 L/min. The relative humidity is set to 90–95% by adjusting the water bath temperature. At 15 L/min, the powder evenly fluidizes the powder bed. Treatment is carried out for approximately 11 hours, by which time the residual acetone level in the powder is reduced to below 250 ppm.

Example 14

General Procedure for Moisture Reduction

The following is a standard general procedure used repeatedly for moisture reduction in pharmaceutical compositions comprising gelatin microspheres:

A similar setup as in Example 12 is employed to reduce the moisture content of the microspheres. In this case, the relative humidity is 35–40%, controlled by setting the water-bath temperature to 2–4° C., and the target range for the final moisture content in the microspheres is 12–18%. The bulk tICAM(453) microspheres are removed from the column and stored in type-III flint glass jars with Teflon®-lined lids at 2–8° C.

Example 15

Process for Making 400 g Gelatin/tICAM(453) Microspheres

Porcine gelatin (type A) was purchased from Hormel Foods (Austin, Minn.). Corn oil and Span 80 (sorbitan monooleate, NF grade) were supplied by Ruger Chemical Co. Inc. (Irvington, N.J.). Acetone (reagent grade) was purchased from EM Science (Gibbstown, N.J.). Purified ICAM was prepared according to Example 1 in a 10 mM histidine buffer pH 7.0 (~50 mg/ml). Human serum albumin (HAS Lot # 684PO67A, commercial stock) was obtained from Bayer Corporation, Biological Products, Clayton, N.C. The vessels, impellers, shafts and baffles used in these experiments were made of Stainless steel (SS 316).

Strategies for a geometric scale up of the manufacturing process from the 150 g scale of Example 8, 9, and 10 to larger scales were based on principles of constant mixing power per unit volume. A geometric scaled-up process from the 150 g to 400 g batch size would involve a proportional increase in vessel size keeping the height to diameter ratio (H/D) of the emulsion bed constant.

The following derivation was used to determine the formula required for calculating geometrically scaled-up process parameters for larger batch sizes based on known process parameters at the smaller 150 g scale.

Geometric scale-up:

Volume of the emulsion bed=$\pi R^2 H$ where R is the radius of the bucket and H is the emulsion height.

Dividing the volume of the emulsion bed at a larger geometrically scaled up batch size ($\pi R_L^2 H_L$) by the emulsion volume at the smaller 150g scale ($\pi R_s^2 H_s$), produces $$\frac{V_L}{V_S} = \frac{\pi R_L^2 H_L}{\pi R_S^2 H_S}$$

Substituting the radius by the bucket diameter (R=D/2)

$$\frac{V_L}{V_S} = \frac{\pi (D_L^2/4) H_L}{\pi (D_S^2/4) H_S}$$

X and ÷ the numerator and denominator by $D_L$ and $D_S$, respectively, produces $$\frac{V_L}{V_S} = \frac{\pi(D_L^2/4)(H_L/D_L)}{\pi(D_S^2/4)(H_S/D_S)}$$

For geometric similarity H/D is constant at all scales, hence the above equation reduces to, $$V_L/V_S = (D_L^3/D_S^3)$$

$$D_L/D_S = (V_L/V_S)^{1/3}$$

$$D_L = (V_L/V_S)^{1/3} D_S \quad (1)$$

where, $D_S$—diameter of the vessel used at the smaller 150 g scale (6.7")

$V_S$—volume of the emulsion at the smaller 150 g scale (3.0 L)

$D_L$—diameter of the vessel at any scale larger than 150 g $V_L$—volume of the emulsion at any scale larger than 150 g Thus, knowing the emulsion volume and vessel diameter at the smaller 150 g scale and the emulsion volume for a larger scale (fixed for a given scale), the vessel diameter to be used for that larger scale ($D_L$) can be determined.

Power per unit volume (P/v):

$$\text{Power } P \propto N^3 d^2 \text{ and} \quad (2)$$

$$\frac{(P/v)L}{(P/v)S} = 1$$

where,

N—mixing speed (rpm)

d—impeller diameter $(P/v)_S$—Mixing power per unit volume generated at the smaller 150 g scale $(P/v)_L$—Mixing power per unit volume to be generated at any scale larger than 150 g.

The power per volume equations describe dimensional and dynamic similarity and are applicable in the turbulent flow regime where the power number is constant for a given impeller design for a wide range of Reynolds numbers [Rushton, J. H., E. W. Costich, H. J. Evereft, Chem. Eng. Progress 46(8):395–404 (1950)].

Equations 1 and 2 were used to calculate the geometric scaled up parameters for various larger scales ranging from 300 to 1000 g. These values are listed in Table XIV and account for a proportionate increase in emulsion volume and impeller diameter to generate a similar mixing power per unit volume within the emulsion as that generated at the 150 g scale:

TABLE XIV

Process parameters for various batch sizes calculated using equations for geometric scale-up and constant mixing power per unit volume

| Scale (g) | 150 | 300 | 400 | 500 | 750 | 1000 |
|---|---|---|---|---|---|---|
| Emulsion volume (L) | 3.0 | 6.0 | 8.0 | 10.0 | 15.0 | 20.0 |
| Bucket diameter (inch) | 6.7 | 8.4 | 9.3 | 10.0 | 11.4 | 12.5 |
| Impeller diameter (inch) | 3.0 | 3.8 | 4.1 | 4.5 | 5.1 | 5.6 |
| Emulsion height (inch) | 5.2 | 6.5 | 7.2 | 7.7 | 8.8 | 9.7 |
| RPM | 425 | 365 | 343 | 327 | 299 | 281 |

In addition, an emulsification system is more complex than a simple mixing process, and increased shear forces are important in addition to mixing forces. Mixing times were not kept constant since they were are dependent on the batch size and rate of cooling.

Emulsification set-up for the scaled up process at the 400 g scale:

The relative amounts of gelatin, oil and Span 80 used in the scaled up process at the 400 g scale are outlined in Table XV. As opposed to the 150 g scale method, this process utilizes the same gelatin to oil ratio for the production of both gelatin microspheres and ICAM/gelatin microspheres.

TABLE XV

Relative amounts of gelatin, oil and Span 80 used for production at the 150 g scale and at the 400 g scale

| Amount of Gelatin (g) | Gelatin:Oil Ratio | Volume of Oil (ml) | Amount of Span 80 (g) |
|---|---|---|---|
| 1. 150 g scale | | | |
| Gelatin Microspheres | | | |
| 150 g (20% solution = 750 ml) | 1:3 | 2250 ml | 22.5 g (1% w/v) |
| ICAM/Gelatin Microspheres (11.5% theoretical loading) | | | |
| 105 g gelatin + 15 g ICAM (20% solution = 600 ml) | 1:4 | 2400 ml | 24.0 (1% w/v) |
| 2. 400 g scale | | | |
| Gelatin Microspheres | | | |
| 400 g (20% solution = 2000 ml) | 1:3 | 6000 ml | 60 g (1% w/v) |
| ICAM/Gelatin Microspheres (11.5% theoretical loading) | | | |
| 354 g gelatin + 46 g ICAM (20% solution = 2000 ml) | 1:3 | 6000 ml | 60.0 (1% w/v) |

The emulsification process at the 400 g scale (8L emulsion volume) required a 9.3" diameter vessel with a 4.0" radial impeller at an initial mixing speed of 343 rpm, as seen in Table XIV. A gelatin solution was prepared at a mixing speed of 200 rpm using a 3" radial impeller in a 3 L stainless steel vessel placed in a water bath maintained at 50° C. A mixture of corn oil and Span 80 was mixed at 250 rpm using a 4" radial impeller in a 12 L stainless steel vessel placed in a water bath maintained at 50° C. The dissolved gelatin solution was added to the oil/Span mixture and the emulsification was performed under various experimental conditions (with and without baffles) and cooling rates (gradual, moderate and rapid) to generate microspheres in the desired 50 $\mu$m size range. Photographs of the emulsion at various points during the emulsification process were captured by an optical microscope (Zeiss, Germany) fitted with a camera attachment (Polaroid Microcam, UK) to evaluate the effect of various process parameters on the size of the emulsion droplets and microspheres generated. The microspheres were acetone washed to remove traces of oil and moisture from the microsphere preparation. The acetone washed microspheres were then vacuum filtered using a Buechner funnel and sieved using a 75 $\mu$m mesh sieve to eliminate large particles and aggregates from the microsphere preparation. This was followed by an acetone removal step performed by fluidizing the powder bed with humidified air (RH-90%) for ~16 hours in a chromatography column. Following acetone removal the moisture level of the microspheres was adjusted to 13–15% by circulating clean air (RH-35%) through the column. The dry microspheres were stored in glass containers.

Emulsification Without Baffles (similar to the 150 g scale process):

The manufacturing process used was similar to that used at the smaller 150 g scale. A 4.0" radial impeller was placed in the top left quadrant and positioned off center at a 12 degree angle to the vertical in a 9.25" diameter vessel.

Emulsification With Baffles:

The emulsion volume (8 L), bucket diameter (9.25") and impeller size (4.0") were the same as that used in the experimental set-up without baffles. In addition, four stainless steel baffles (10 inches high and ¾" wide) were positioned vertically and equidistant (90° apart) from each other and ⅜" inches from the sides of the vessel. The impeller was positioned at the center (straight, no angle) of the vessel as seen in FIG. 3b.

Cooling Methods:

Three cooling methods were evaluated as described below:

Gradual Cooling:

The cooling process used was similar to that used at the smaller 150 g scale. The gelatin solution (50° C.) was added to the vessel containing the oil/Span mixture (placed in a 50° C. water bath) and mixed at the preset initial mixing speed. Immediately following addition, the water bath set-point temperature was changed from 50 to 10° C. and the mixing speed was increased as the emulsion gradually cooled to 10° C.

A gradual cooling rate was evaluated for emulsification runs with and without baffles. For emulsification runs performed without baffles, three initial mixing speeds of 343, 375 and 415 rpm were utilized. Experiments with baffles were evaluate at two initial mixing speeds of 425 and 475 rpm.

Moderate Cooling:

Experiments were performed in an attempt to achieve a higher cooling rate (~1.0 deg./min) than that achieved at the 150 g scale (~0.47 deg./min). The gelatin solution (50° C.) was added to the oil/Span mixture (50° C.) and mixed at the preset initial mixing speed. Immediately following addition, the bath was turned off, and ice was gradually added to the warm bath water at intervals to maintain a cooling rate of 1.0 deg./min. Moderate cooling was performed with baffles, and evaluated for two initial mixing speeds of 625 and 640 rpm.

Rapid Cooling:

A rapid cooling rate (~2.3 deg./min) was achieved as follows. Immediately following the addition of the gelatin solution to the oil/Span mixture at 50° C., the initial mixing speed was increased to a predetermined rpm. The emulsion was mixed at this speed for a fixed time (20–40 min) at 50° C. to generate droplets in the 50 μm size range. The emulsion was then rapidly cooled to 15° C. by draining the warm water from the water bath and replacing it with a slurry of ice and water. The bath temperature was set to 0.1° C. The mixing speed was increased as the emulsion rapidly cooled from 50 to 15° C. When the emulsion reached a temperature of 15° C., the bath temperature was increased to 10° C. and the microspheres were held at this temperature and stirred for 1 hour at 525 rpm.

The rapid cooling process with baffles was utilized to produce gelatin microspheres, albumin-loaded gelatin microspheres, and ICAM-loaded gelatin microspheres under the following two experimental conditions:

High Mixing Speed:

The impeller was positioned at a height of 1.5 " from the bottom of the vessel, and three initial mixing speeds of 600, 625 and 650 rpm were evaluated, with a final mixing speed of 780 rpm. In addition, initial mixing times of 20, 30 and 40 minutes at 650 rpm were tested.

Low Mixing Speed:

In order to decrease the mixing speed and still generate emulsion droplets in the desired size range (~50 μm) the impeller was raised to 2.5" from the bottom, and an initial mixing speed of 425 rpm with a final rpm of 605 during cooling was evaluated.

Studies on release of ICAM from gelatin microspheres:

Release studies on ICAM/gelatin microspheres were performed as follows: 20 mg of ICAM/gelatin microspheres were weighed into a 12×75 mm polypropylene test tube and 2.0 ml of phosphate buffered saline (pH 7.2) was added to the tube. The tube was vortexed briefly to suspend the microspheres and was placed in a 40° C. water bath. The tube was vortexed at intervals of 5 minutes for a total of 1.0 hr. The resulting solution was filtered through a syringe filter (0.2 μm, 25 mm Gelman Acrodisk (Fisher Scientific, Norcross, Ga.), low protein binding membrane) and submitted in duplicate for ICAM determination by immunonephelometry Emulsification set-up for the scaled up process at the 400 g scale:

Gelatin microspheres and ICAM/gelatin microspheres were prepared by an emulsification process carried out in a 9.25" diameter vessel with a 4" radial impeller at a predetermined initial mixing speed, under various experimental conditions (with and without baffles) utilizing several cooling methods (gradual, moderate and rapid cooling). The results obtained under these varying conditions are summarized below.

Emulsification without baffles (Gradual Cooling):

Three emulsification runs with initial mixing speeds of 343, 375 and 415 rpm were evaluated. The maximum initial mixing speed that was possible without causing excessive splashing and air entrapment was 415 rpm. The lowest mixing speed of 343 rpms with a 4" radial impeller was determined by geometric scale-up calculations (values listed in Table XIV) and provided similar mixing conditions as that obtained at the 150 g batch (6.7" diameter vessel, 3.0" impeller and an initial mixing speed of 425 rpm).

The results for the above three runs are outlined in Table XVI:

TABLE XVI

Experimental conditions and particle size data for microspheres prepared by the batch emulsification process utilizing gradual cooling (a) without baffles, and (b) with baffles (a) Gradual cooling without baffles

| Impeller Position | 12 deg | 12 deg. | 12 deg. |
|---|---|---|---|
| Baffles | NO | NO | NO |
| RPM | 343 | 375 | 415 |
| Cooling Rate | Gradual | Gradual | Gradual |
| Particle Size, μm | 83 | 72 | 71 |
| Span | 0.86 | 0.82 | 0.81 |
| % < 10 μm | 0 | 0 | 0 |
| % > 100 μm | 21 | 11 | 9 |

(b) Gradual cooling with baffles

| Impeller Position | Center | Center |
|---|---|---|
| Baffles | YES | YES |
| RPM | 425 | 475 |
| Cooling Rate | Gradual | Gradual |
| Particle Size, μm | 65 | 70 |
| Span | 0.78 | 0.67 |
| % < 10μm | 0 | 0 |
| % > 100 μm | 6 | 9 |

TABLE XVI-continued Experimental conditions and particle size data for microspheres prepared by the batch emulsification process utilizing gradual cooling (a) without baffles, and (b) with baffles Gradual Cooling Rate ~ 0.25 deg./min The average particle size of the microspheres generated by all three runs was large (>70 μm), which were much higher than the acceptable product specification of ~50 μm. The larger emulsion volume (8 L) at the 400 g scale required ~2.5 hr to gradually cool from 50 to 15° C. This corresponded to a cooling rate of 0.25° C./min which was much slower than 0.47° C./min observed at the 150 g scale (3 L emulsion volume). During this slow cooling period, the three mixing speeds evaluated were insufficient to provide the shear necessary to produce and maintain small emulsion droplets. These droplets coalesced to large droplets, which on cooling resulted in large particles. In addition a high percentage (10–20%) of the microspheres was above 100 μm, which was outside the acceptable limit of <10%. No microspheres below 10 μm were generated by this process.

The principles of geometric scale-up and constant mixing power per unit volume assume that the mixing process dictates the particle size of the microspheres. However, the experiments performed thus far demonstrate that droplet coalescence during cooling (due to low shear rates) and the low cooling rates are important factors affecting particle size. These two issues were addressed by utilizing baffles and a rapid cooling rate, as described below.

Emulsification with baffles:

A high shear rate associated with a high mixing speed could not be achieved without a secondary source to enhance turbulence and shear in the system. Baffles were used to increase the mixing speed and shear in the system during the emulsification step to produce smaller droplets and subsequently smaller microspheres. A schematic representation of the batch emulsification process with baffles can be seen in FIG. 4. Higher initial mixing speeds up to 650 rpms with minimal splashing and air entrapment were achieved using baffles.

The emulsification process with baffles was evaluated using three different cooling methods.

Gradual cooling (baffles):

The microspheres prepared possessed average diameters >65 μm (Table 3XVIb). Photographs of the emulsion droplets and resulting microspheres at various stages during the process can be seen in FIG. 6. Emulsion droplets in the desired size range (~50 μm) were achieved during the emulsification process due to the higher shear rates achieved with baffles. However, during the long cooling period the emulsion droplets coalesced to form larger emulsion droplets which, on cooling, resulted in large microspheres (>65 μm).

The above experiments demonstrated that a slow cooling rate of ~0.25 deg./min was not successful in producing 50 μm microspheres. Subsequent experiments (moderate and rapid cooling) investigated higher cooling rates.

Moderate cooling:

A moderate cooling rate of 1.0 deg./min also resulted in droplet coalescence and large particles (>135 μm) and ~80% of the particles above 100 μm. These results are summarized in Table XVII:

TABLE XVII

Experimental conditions and particle size data for microspheres prepared by the batch emulsification process utilizing manually controlled cooling with baffles

| Impeller Position | Center | Center |
|---|---|---|
| Baffles | YES | YES |
| RPM | 625 | 640 |
| Cooling Rate | Moderate | Moderate |
| Particle Size, μm | 138 | 144 |
| Span | 0.85 | 0.87 |
| % < 10 μm | 0 | 0 |
| % > 100 μm | 81 | 83 |

Moderate Cooling Rate ~ 1.0 deg./min

FIG. 7 shows the appearance of the emulsion droplets and solid microspheres at various stages during the moderate cooling process. Emulsion droplets in the desired size range (~50 μm) were achieved during the emulsification step, with a higher mixing speed of 625 rpm. However, during the cooling from 50 to 15° C. (35 min) the small emulsion droplets coalesced to yield large microspheres. A higher initial mixing speed could have resulted in smaller droplets which were thermodynamically unstable resulting in a greater degree of coalescence. This could explain the higher particle sizes and greater percentages of particles above 100 μm seen in the moderate cooling process (Table XVII) over that observed using the gradual cooling process (Table XVI).

In an attempt to gel the ~50 μm emulsion droplets into 50 μm microspheres rapidly, thus preventing them from coalescing, a rapid cooling method was evaluated.

Rapid cooling:

A rapid cooling rate of ~2.3 deg./min was achieved under two different experimental conditions (high mixing and low mixing), as described earlier. The emulsion cooled from 50 to 15° C. in ~15 min.

High Mixing Speed:

Three initial emulsification speeds of 600, 625 and 650 rpms were evaluated. An emulsification time of 20 min at the above mixing speeds produced droplets in the 50 μm size range, which were rapidly cooled to generate microspheres that possessed average particle volume diameters of 57 μm, 60, 69 and 62 μm, no fines, and less than 10% of the particles above 100 μm. These results are summarized in Table XVIII:

TABLE XVIII

Experimental conditions and particle size data for gelatin microspheres prepared by the batch emulsification process utilizing the rapid cooling method with baffles and (a) an initial emulsification time of 20 and 40 minutes, and (b) an initial emulsification time of 30 min.

(a) Initial emulsification times of 20 and 40 min

| | Gelatin Microspheres | | | | |
|---|---|---|---|---|---|
| Emulsification time | 20 min | 20 min | 20 min | 20 min | 40 min |
| Impeller Position | Center | Center | Center | Center | Center |
| Baffles | YES | YES | YES | YES | YES |
| RPM | 600 | 625 | 625 | 650 | 650 |
| Cooling Rate | Rapid | Rapid | Rapid | Rapid | Rapid |
| Particle Size, μm | 57 | 60 | 69 | 62 | 63 |
| Span | 0.92 | 0.85 | 0.87 | 0.79 | 0.86 |
| % <10 μm | 0 | 0 | 0 | 0 | 0 |
| % >100 μm | 5 | 4 | 9 | 5 | 6 |

TABLE XVIII-continued

Experimental conditions and particle size data for gelatin microspheres prepared by the batch emulsification process utilizing the rapid cooling method with baffles and (a) an initial emulsification time of 20 and 40 minutes, and (b) an initial emulsification time of 30 min.

(b) initial emulsification time of 30 min

| | Gelatin Microspheres | | |
|---|---|---|---|
| Emulsification time | 30 min | 30 min | 30 min |
| Impeller Position | Center | Center | Center |
| Baffles | YES | YES | YES |
| RPM | 650 | 650 | 650 |
| Cooling Rate | Rapid | Rapid | Rapid |
| Particle Size, μm | 56.71 | 52.75 | 55.43 |
| Span | 0.81 | 0.79 | 0.78 |
| % <10 μm | 0 | 0 | 0 |
| % >100 μm | 3 | 2 | 2 |

Rapid Cooling Rate~2.3 deg/min

The process to be transferred to the pilot plant required a range of initial emulsification times to be specified, rather than a rigid 20 min mixing time. The minimum emulsification time required to generate ~50 μm emulsion droplets prior to rapid cooling, was 20 min. This process was repeated for an emulsification time of 40 min, followed by rapid cooling which generated particles with a size of 63 μm (Table XVIIIa).

Since the process worked at 20 and 40 min., an initial emulsification time of 30 ±10 min. at 650 rpm could be specified. Three replicates performed with a 30 min. emulsification time followed by rapid cooling resulted in average particles sizes of ~55 μm. These summarized in Table XVIIb.

This process can be summarized as follows:

| Time | Emulsion Temp. (° C.) | RPM | |
|---|---|---|---|
| | 50 | 375 | Gelatin added to oil |
| 0 | 50 | 650 | |
| 10 | 50 | 650 | |
| 20 | 50 | 650 | |
| 30 | 50 | 650 | |

The emulsion generated was rapidly cooled as describe earlier. During the cooling process, the rpms were increased at set temperatures as indicated below.

| Emulsion Temp. (° C.) | RPM |
|---|---|
| 40 | 700 |
| 35 | 715 |
| 30 | 730 |
| 28 | 750 |
| 23 | 765 |
| 18 | 780 |
| 15 | 780 |

The microspheres were then acetone washed, filtered and dried.

Albumin/gelatin microspheres generated by the above process possessed average sizes of 61, 58 and 70 μm, and ICAM/gelatin microspheres were 66 μm in volume diameter. The results are summarized in Table XIX and shown in FIG. 8:

TABLE XIX

Experimental conditions and particle size data for Albumin/Gelatin microspheres and ICAM/gelatin microspheres prepared by the batch emulsification process utilizing the rapid cooling method with baffles

| | Albumin/Gelatin Microspheres | | | ICAM/Gelatin Microspheres |
|---|---|---|---|---|
| | Center | Center | Center | Center |
| Impeller Position | 1.5" from base | 1.5" from base | 1.5" from base | 1.5" from base |
| Emulsification time | 30 min | 30 min | 30 min | 30 min |
| Baffles | YES | YES | YES | YES |
| RPM | 650 | 650 | 650 | 650 |
| Cooling Rate | Rapid | Rapid | Rapid | Rapid |
| Particle Size, μm | 61 | 58 | 70 | 66 |
| Span | 0.70 | 0.70 | 0.75 | 0.84 |
| % < 10 μm | 0 | 0 | 0 | 0 |
| % > 100 μm | 3 | 2 | 8 | 8 |

Rapid Cooling Rate ~ 2.3 deg/min

Low mixing speed:

The high mixing speed process resulted in splashing during the emulsification process, and air entrapment during the holding step (780 rpm for 1 hr at 15° C.). To minimize splashing, the impeller was raised to 2.5" from the bottom of the vessel and was used at a lower mixing speed. The initial mixing speed evaluated was 425 rpm with a final rpm of 605 during the cooling process.

The process evaluated was as follows:

| Time (min) | Emulsion Temp. (° C.) | RPM | |
|---|---|---|---|
| | 50 | 375 | Gelatin added to oil |
| 0 | 50 | 425 | |
| 10 | 50 | 425 | |
| 20 | 50 | 425 | |
| 30 | 50 | 425 | |

The emulsion generated was rapidly cooled as describe earlier. As the emulsion cooled, the rpms were increased at set temperatures as indicated below.

| Emulsion Temp. (° C.) | RPM |
|---|---|
| 45 | 475 |
| 40 | 525 |
| 35 | 550 |
| 30 | 575 |
| 25 | 590 |
| 20 | 605 |
| 15 | 605 |

The microspheres were then acetone washed, filtered and dried.

Gelatin microspheres, albumin/gelatin microspheres, and ICAM/gelatin microspheres (varying loads) prepared by the low mixing speed process were in 50 m size range, with spans of around 0.8, no fines below 10 μm, and less than 3.5% above 100 μm. These results are summarized in Tables XX and XXI and shown in FIG. 9:

TABLE XX

Experimental conditions and particle size data for gelatin microspheres and albumin/gelatin microspheres prepared by the batch emulsification process utilizing the modified rapid cooling process with baffles

|  | Gelatin Microspheres | | Albumin/Gelatin Microspheres | |
|---|---|---|---|---|
| Impeller Position | Center 2.5" from base | Center 2.5" from base | Center 2.5" from base | Center 2.5" from base |
| Baffles | YES | YES | YES | YES |
| RPM | 425 | 425 | 425 | 425 |
| Cooling Rate | Rapid | Rapid | Rapid | Rapid |
| Particle Size, μm | 53 | 50 | 55 | 54 |
| Span | 0.89 | 0.81 | 0.80 | 0.75 |
| % < 10 μm | 0 | 0 | 0 | 0 |
| % > 100 μm | 2 | 1 | 2 | 2 |

TABLE XXI

Experimental conditions and particle size data for ICAM/gelatin microspheres prepared by the batch emulsification process utilizing the modified rapid cooling process with baffles

| | ICAM/Gelatin Microspheres | | | | |
|---|---|---|---|---|---|
| % loading of ICAM | 10% | 10% | 10% | 5% | 1% |
| Impeller Position | Center 2.5" from base | Center 2.5" from base | Center 2.5" from base | Center 2.5" from base | Center 2.5" from base |
| Baffles | YES | YES | YES | YES | YES |
| RPM | 425 | 425 | 425 | 425 | 425 |
| Cooling Rate | Rapid | Rapid | Rapid | Rapid | Rapid |
| Particle Size, μm | 54 | 57 | 58 | 54 | 52 |
| Span | 0.76 | 0.75 | 0.84 | 0.82 | 0.86 |
| % <10 μm | 0 | 0 | 0 | 0 | 0 |
| % >100 μm | 1 | 2 | 3 | 2 | 2 |

Typical particle sizes of microspheres obtained by this process are shown in Table XXII and FIG. 10:

TABLE XXII

Typical particle sizes obtained by the above process

| Size (Low) μm | Result in % | Size (Hi) μm | Result Below % |
|---|---|---|---|
| 0.50 | 0.00 | 1.32 | 0.00 |
| 1.32 | 0.00 | 1.60 | 0.00 |
| 1.60 | 0.00 | 1.95 | 0.00 |
| 1.95 | 0.00 | 2.38 | 0.00 |
| 2.38 | 0.00 | 2.90 | 0.00 |
| 2.90 | 0.00 | 3.53 | 0.00 |
| 3.53 | 0.00 | 4.30 | 0.00 |
| 4.30 | 0.00 | 5.24 | 0.00 |
| 5.24 | 0.00 | 6.39 | 0.00 |
| 6.39 | 0.00 | 7.78 | 0.00 |
| 7.78 | 0.00 | 9.48 | 0.00 |
| 9.48 | 0.00 | 11.55 | 0.00 |
| 11.55 | 0.00 | 14.08 | 0.00 |
| 14.08 | 0.00 | 17.15 | 0.00 |
| 17.15 | 0.26 | 20.90 | 0.25 |
| 20.90 | 1.32 | 25.46 | 1.57 |
| 25.46 | 3.04 | 31.01 | 4.61 |
| 31.01 | 7.27 | 37.79 | 11.88 |
| 37.79 | 16.58 | 46.03 | 28.45 |
| 46.03 | 27.01 | 56.09 | 55.46 |
| 56.09 | 24.35 | 68.33 | 79.82 |
| 68.33 | 12.82 | 83.26 | 92.64 |
| 83.26 | 5.21 | 101.44 | 97.85 |
| 101.44 | 1.77 | 123.59 | 99.62 |
| 123.59 | 0.37 | 150.57 | 100.00 |
| 150.57 | 0.00 | 183.44 | 100.00 |
| 183.44 | 0.00 | 223.51 | 100.00 |
| 223.51 | 0.00 | 272.31 | 100.00 |
| 272.31 | 0.00 | 331.77 | 100.00 |
| 331.77 | 0.00 | 404.21 | 100.00 |
| 404.21 | 0.00 | 492.47 | 100.00 |
| 492.47 | 0.00 | 600.00 | 100.00 |

As can be seen from the particle size table the average particle size [D(4,3)] is 56.36 μm, with a span of 0.78, no particles with a volume particle diameter <10 μm, and ≈3% particles with a volume particle diameter above 100 μm.

Studies on release of ICAM from Gelatin microspheres:

ICAM/gelatin microspheres prepared with varying theoretical loads of 12.5, 10.5, 10.0, 5.0, 2.5 and 1.5% were dissolved as described above in this example, and assayed for ICAM by immunonephelometry. All batches exhibited ~100% actual loading, within assay variability. A ICAM/gelatin microsphere preparation was dissolved, and the sample bioassayed. The ICAM/gelatin microsphere formulation was comparable to ICAM standard (103% of standard). The $ED_{50}$ was 0.298 compared to 0.303 for the standard. These results indicated that ICAM was still potent following the formulation and washing procedures.

Conclusions:

The strategy for scaling up the microsphere manufacturing process to the 400 g scale was a geometric scale-up with constant mixing power per unit volume, based on a water-in-oil emulsification process developed at the smaller 150 g scale. Several experimental conditions (with and without baffles) and various cooling methods (gradual, moderate, and rapid) were evaluated. The gradual cooling process without baffles required ~2.5 hr to cool from 50 to 15° C. The mixing speeds evaluated (343, 375 and 415 rpm) did not provide the shear necessary to produce and maintain small emulsion droplets, which on cooling resulted in large microspheres. The mixing speed could not be increased above 415 rpm without causing significant splashing and air entrapment. Baffles were introduced into the system to increase the mixing speed and shear forces in the system. The emulsification speeds were increased to 650 rpm resulting in emulsion droplets in the 50 m size range. However, during the gradual (2.5 hr cooling time) and moderate cooling (35 min cooling time) steps these 50 μm emulsion droplets coalesced, which on cooling, resulted in very large particles. A rapid cooling process was developed to gel the 50 μm emulsion droplets rapidly before they coalesced. This process was evaluated under two conditions; a high mixing speed with a low impeller height and a low mixing speed at a higher impeller height. Both methods consistently produced microspheres in the 50 μm size range. Three factors were identified as critical for achieving microspheres in the desired 50 μm size range. The include; initial emulsification time (~30 min), appropriate vessel geometry and mixing speeds, and a rapid cooling rate (~2.3 deg./min).

Numerous modifications and variations in the invention as described in the above illustrative examples are expected to occur to those skilled in the art and consequently only those limitations as appear in the appended claims should be placed thereon.

Accordingly it is intended in the appended claims to cover all such equivalent variations which come within the scope of the invention as claimed.

What is claimed is:

1. A process for making an intranasal drug delivery system comprising gelatin microspheres in combination with a drug intended for intranasal delivery, said process comprising:

a) preparing a low-salt or salt-free aqueous solution of gelatin and the drug to be delivered, at a temperature above the gelation temperature of the gelatin;

b) preparing a solution of a suitable oil and a suitable surfactant;

c) emulsifying a mixture of the solution of step (a) and the solution of step (b) to generate a water-in-oil emulsion wherein the volume ratio of (a):(b) is between 1:2 and 1:10;

d) continuing emulsification until the target droplet size is achieved;

e) reducing the temperature of said emulsion to below the gelation temperature of the gelatin at a controlled rapid rate to achieve gelation before droplet coalescence, thus allowing the formation of gelatin microspheres associated with drug at the desired particle size;

the emulsion in steps (c, d) and (e) above being mixed at the maximum rate consistent with a low-vortex or vortex-free circulation pattern;

f) separating the drug-containing microspheres from the oil/surfactant phase; and g) dehydrating the drug-containing microspheres to produce a dry powder.

2. The process of claim 1 wherein said gelatin in step (1a) has a Bloom strength of approximately 250.

3. The process of claim 1 wherein said oil in step (1b) is vegetable oil.

4. The process of claim 1 wherein said surfactant in step (1b) has a hydrophilic-lipophylic balance of 4–6.

5. The process of claim 1 wherein said volume ratio in step (1c) is between 1:3 and 1:4.

6. The process of claim 1 wherein said droplet size in step (1d) is 20–80 $\mu$m.

7. The process of claim 6 wherein said droplet size in step (1d) is 40–60 $\mu$m.

8. The process of claim 1 wherein the temperature is reduced in step (1e) at the rate of 2.0–2.5° C./min.

9. The process of claim 1 wherein said drug-containing microspheres are removed from the oil/surfactant phase by washing with a water-miscible solvent.

10. The process of claim 1 wherein said drug-containing microspheres are removed from the oil/surfactant phase by washing with hydrocarbon solvent, followed by washing with a water-miscible solvent.

11. The process of claim 1 wherein said drug is ICAM-1 or a fragment, analog, or derivative thereof.

12. The process of claim 1 wherein said process is a batch process.

13. The process of claim 1 wherein said process is a continuous process.

14. A process for removing residual solvent from a pharmaceutical matrix, comprising contacting said pharmaceutical matrix with a humidified gas under conditions which permit residual solvent to be entrained in the gas, and removing the gas.

15. The process of claim 14 wherein said pharmaceutical matrix is a dry powder.

16. The process of claim 15 wherein said humidified gas is passed through said dry powder under conditions which create a fluidized bed in the dry powder.

17. The process of claim 16 wherein said fluidized bed is contained in a column having a filter at each end which is permeable to the humidified gas but not permeable to the dry powder.

18. The process of claim 16 wherein said dry powder comprises gelatin microspheres.

19. The process of claim 18 wherein said gelatin microspheres encapsulate a drug.

20. The process of claim 19 wherein said drug is ICAM-1 or a fragment, analog or derivative thereof.

21. The process of claim 1 wherein residual solvent is removed from the resulting microspheres by means of the process of claim 14.

22. The process of claim 21 wherein said drug is ICAM-1 or a fragment, analog or derivative thereof.

23. The product of the process of claim 1 wherein said drug is ICAM-1 or a fragment, analog, or derivative thereof.

24. The product of the process of claim 14 wherein said drug is ICAM-1 or a fragment, analog, or derivative thereof.

25. The product of the process of claim 21 wherein said drug is ICAM-1 or a fragment, analog, or derivative thereof.

* * * * *